United States Patent
Di Scala et al.

(10) Patent No.: US 9,360,481 B2
(45) Date of Patent: Jun. 7, 2016

(54) PREDICTIVE BIOMARKER FOR CANCER TREATMENT WITH ADCC-ENHANCED ANTIBODIES

(71) Applicant: Roche Glycart AG, Schlieren (CH)

(72) Inventors: Lilla Di Scala, Basel (CH); Stefan Evers, Muellheim (DE); Christian Gerdes, Erlenbach/ZH (CH); Christoph Mancao, Weil am Rhein (DE); Alexandre Passioukov, Zuerich (CH); Pablo Umana, Wollerau (CH)

(73) Assignee: Roche Glycart AG, Schlieren (CH)

( * ) Notice: Subject to any disclaimer, the term of this patent is extended or adjusted under 35 U.S.C. 154(b) by 0 days.

(21) Appl. No.: 14/159,895

(22) Filed: Jan. 21, 2014

(65) Prior Publication Data

US 2014/0227256 A1 Aug. 14, 2014

(30) Foreign Application Priority Data

Jan. 23, 2013 (EP) ..................................... 13152293

(51) Int. Cl.
| | | |
|---|---|---|
| *A61K 39/395* | (2006.01) | |
| *G01N 33/53* | (2006.01) | |
| *G01N 33/574* | (2006.01) | |
| *C07K 16/30* | (2006.01) | |

(52) U.S. Cl.
CPC .......... *G01N 33/57492* (2013.01); *C07K 16/30* (2013.01); *G01N 33/574* (2013.01); *G01N 2333/7051* (2013.01); *G01N 2333/70535* (2013.01); *G01N 2800/52* (2013.01)

(58) Field of Classification Search
None
See application file for complete search history.

(56) References Cited

U.S. PATENT DOCUMENTS

| | | |
|---|---|---|
| 2010/0167315 A1 | 7/2010 | Thibault et al. |
| 2010/0247484 A1 | 9/2010 | Barchet et al. |

FOREIGN PATENT DOCUMENTS

| | | |
|---|---|---|
| WO | 2012/038068 | 3/2012 |
| WO | 2013/113641 | 8/2013 |
| WO | 2013/127465 | 9/2013 |

OTHER PUBLICATIONS

Varchetta et al (Cancer Res, 2007, 67(24): 11991-11999).*
Shimizu et al (Cancer Research, 1991, 51: 6153-6162).*
Yoshino et al (Lung Cancer, 1993, 10(1-2): Abstract).*
Al-Shibli et al., "Prognostic effect of epithelial and stromal lymphocyte infiltration in non-small cell lung cancer" Clin Cancer Res. 14(16):5220-7 (Aug. 2008).
Badoual et al., "Prognostic value of tumor-infiltrating CD4+ T-cell subpopulations in head and neck cancers" Clin Cancer Res. 12(2):465-72 (2006).
Brandwein-Gensler et al., "Oral squamous cell carcinoma: histologic risk assessment, but not margin status, is strongly predictive of local disease-free and overall survival" Am J Surg Pathol. 29(2):167-78 (Feb. 2005).
Dieu-Nosjean et al., "Long-term survival for patients with non-small-cell lung cancer with intratumoral lymphoid structures" J Clin Oncol. 26(27):4410-7 (2008).
Evers et al., "Exploratory Biomarker Program for RG7160 (GA201) in the PhaseI-II Clinical Trials" Abstract Symposium on Cancer Immunology and Immunotherapy, Nutley, NJ. USA, (Sep. 12, 2011).
Fridman et al., "Immune infiltration in human cancer: prognostic significance and disease control" Curr Top Microbiol Immunol. 344:1-24 (2011).
Galon et al., "Type, density, and location of immune cells within human colorectal tumors predict clinical outcome" Science 313:1960-4 (Sep. 2006).
Gregoire et al., "The Trafficking of Natural Killer Cells" Immunological Revews 220:169-182 (2007).
Halama et al., "Localization and density of immune cells in the invasive margin of human colorectal cancer liver metastases are prognostic for responcse to chemotherapy" Cancer Res. 71(17):5670-7 (2011).
Halama et al., "Natural killer cells are scarce in colorectal carcinoma tissue despite high levels of chemokines and cytokines" Clin Cancer Res. 17(4):678-89 (Feb. 2011).
Halama et al., "The local immunological microenvironment in colorectal cancer as a prognostic factor for treatment decisions in the clinic: The way ahead" Oncoimmunology 1(1):62-66 (2012).
Hiraoka et al., "Concurrent infiltration by CD8+ T cells and CD4+ T cells is a favourable prognostic factor in non-small-cell lung carcinoma" Br J Cancer 94(2):275-80 (Jan. 2006).
IPRP for PCT/EP2014/051034.
Kawai et al., "Predominant infiltration of macrophages and CD8(+) T Cells in cancer nests is a significant predictor of survival in stage IV nonsmall cell lung cancer" Cancer 113(6):1387-95 (Sep. 2008).
Le et al., "Galectin-1: a link between tumor hypoxia and tumor immune privilege" J Clin Oncol. 23(35):8932-41 (2005).
Luis Paz-Ares et al., "Phase 1 Pharmacokinetic and Pharmacodynamic Dose-Escalation Study of RG7160 (GA201), the First Glycoengineered Monoclonal Antibody Against the Epidermal Growth Factor Receptor, in Patients with Advanced Solid Tumors" Journal of Clinical Oncology 29(28):3783-3790 (2011).
Marcus et al., "Prognostic factors in oral cavity and oropharyngeal squamous cell carcinoma" Cancer 101(12):2779-87 (2004).
Marechal et al., "Putative contribution of CD56 positive cells in cetuximab treatment efficacy in first-line metastatic colorectal cancer patients" BMC Cancer 10(340):1-11 (Jun. 30, 2010).

(Continued)

*Primary Examiner* — Sean Aeder

(57) ABSTRACT

The present invention is directed to methods for identifying which patients diagnosed with cancer will most benefit from treatment with an anti-cancer therapy comprising an ADCC-enhanced antibody.

7 Claims, 7 Drawing Sheets

(56) References Cited

OTHER PUBLICATIONS

Pages et al., "Effector memory T cells, early metastasis, and survival in colorectal cancer" N Engl J Med. 353(25):2654-66 (2005).
PCT ISR for PCT/EP2012/053600.
PCT Written Opinion for PCT/EP2012/053600.
Rajjoub et al., "Prognostic significance of tumor-infiltrating lymphocytes in oropharyngeal cancer" Ear Nose Throat J. 86(8):596-11 (2007).
Schleypen et al., "Cytotoxic markers and frequency predict functional capacity of natural killer cells infiltrating renal cell carcinoma" Clin Cancer Res. 12(3 Pt 1):718-25 (2006).
Sconocchia et al., "Tumor infiltration by FcγRIII (CD16)+ myeloid cells is associated with improved survival in patients with colorectal carcinoma" Int J Cancer 128(11):2663-72 (2011).
Scott, A. M. et al., "Immunological effects of chimeric anti-GD3 monoclonal antibody KM871 in patients with metastatic melanoma" Cancer Immunity 5(3):1-12 (2005).
Shimizu, Y. et al., "Characterization of Human Autotumor-Reactive T-Cell Clones Obtained from Tumor-infiltrating Lymphocytes in Liver Metastasis of Gastric Carcinoma1" Cancer Research 51(22):6153-6162 (1991).
T. Maruyama et al., "Immunonutritional Diet Modulates Natural Killer Cell Activation and Th17 Cell Distribution in Patients with Gastric and Esophageal Cancer" Nutrition 27:146-152 (2011,).
Varchetta et al., "Elements related to heterogeneity of antibody-dependent cel cytotoxicity in patients under trastuzumab therapy for primary operable breast cancer overexpressing Her2" Cancer Res. 67(24):11991-9 (2007).
W.L. Gluck et al., "Phase 1 Studies of Interleukin (IL)-2 and Rituximab in B-Cell Non-Hodgkin's Lymphoma: IL-2 Mediated Natural Killer Cell Expansion Correlations with Clinical Response" Clinical Cancer Research 10:2253-2264 (2004).
Welsh et al., "Macrophage and mast-cell invasion of tumor cell islets confers a marked survival advantage in non-small-cell lung cancer" J Clin Oncol. 23(35):8959-67 (Dec. 2005).
Wilson et al., "Il-2 mediated NK cell expansion correlates with clinical response to rituximab: Results of two phase I trials of the combination of IL-2 and rituximab" Blood, American Society Of Hematology, US 98(11):602a (Nov. 16, 2001).
Yoshino, I. et al., "Phenotypes of lymphocytes infiltrating non-small cell lung cancer tissues and its variation with histological types of cancer" Lung Cancer 10(1-2):13-19 (1993).
Zhang et al., "Different subsets of tumor infiltrating lymphocytes correlate with NPC progression in different ways" Mol Cancer 9:4 (Jan. 2010).
Zhang et al., "Intratumoral T cells, recurrence, and survival in epithelial ovarian cancer" N Engl J Med. 348(3):203-13 (2003).

\* cited by examiner

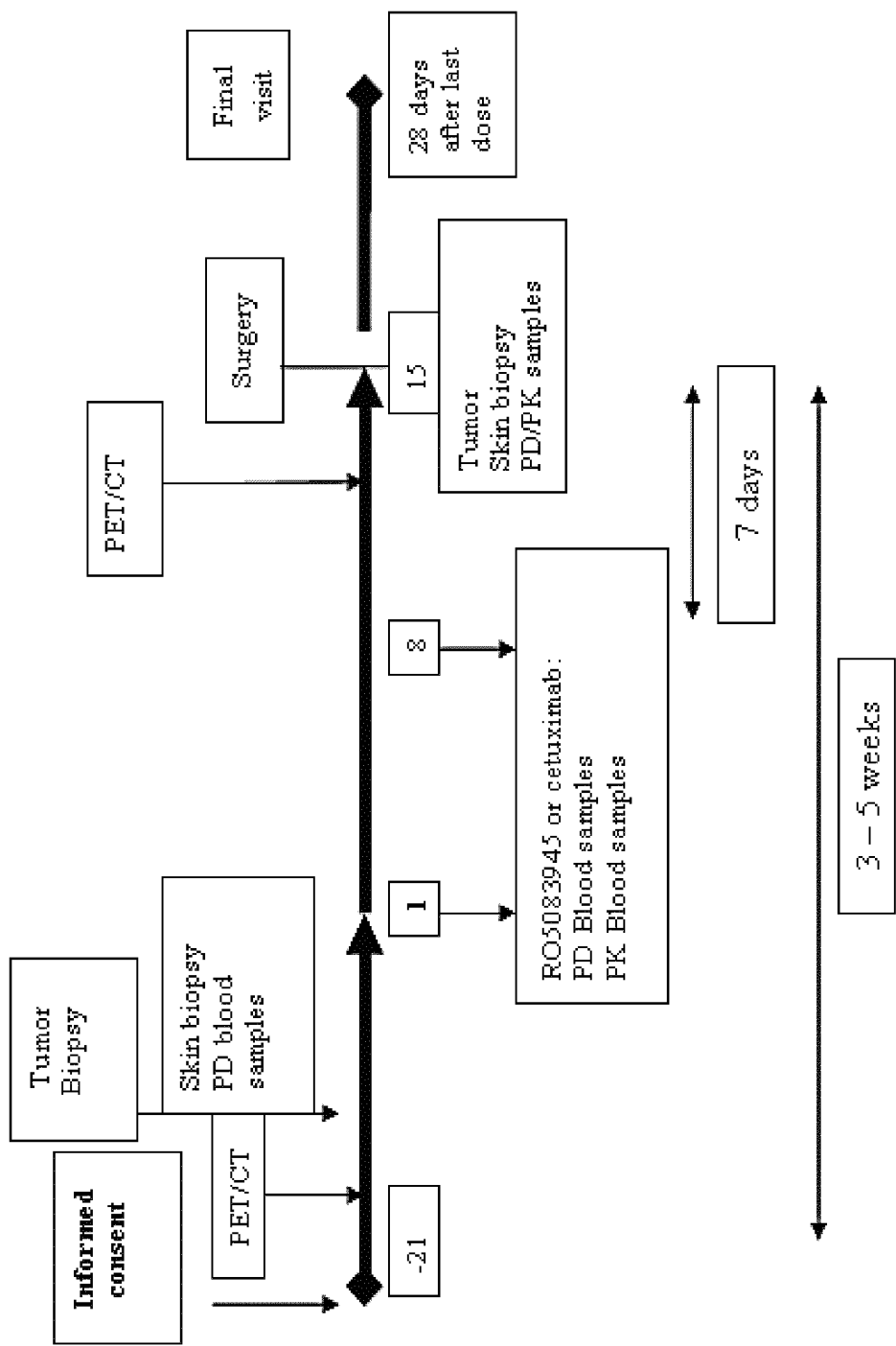

PREDICTIVE BIOMARKER FOR CANCER TREATMENT WITH ADCC-ENHANCED ANTIBODIES

CROSS REFERENCE TO RELATED APPLICATIONS

This application claims priority to European Patent Application No. EP 13152293.0 filed Jan. 23, 2013, the disclosure of which is incorporated herein by reference in its entirety.

SEQUENCE LISTING

The present application contains a Sequence Listing which has been submitted in ASCII format via EFS-Web and is hereby incorporated by reference in its entirety. Said ASCII copy, created on Jan. 13, 2014, is named P5613 US_ST25.txt and is 6,465 bytes in size.

FIELD OF THE INVENTION

The present invention is directed to methods for identifying which patients diagnosed with cancer will most benefit from treatment with an anti-cancer therapy comprising an ADCC-enhanced antibody.

BACKGROUND OF THE INVENTION

Antibodies with enhanced ADCC capacity are an emerging species in the field of cancer therapy. It has been recognized that the so-called effector functions of an antibody, which are mediated by its Fc region, are an important mechanism of action in antibody-based cancer therapy. Of particular importance in this context is antibody-dependent cellular cytotoxicity (ADCC), the destruction of antibody-coated target cells (e.g. tumor cells) by NK (natural killer cells) and other immune effector cells, which is triggered when antibody bound to the surface of a cell interacts with activating Fc receptors on the effector cell.

Enhancing the ADCC activity of therapeutic antibodies has therefore become of great interest and various methods for ADCC enhancement have been described. For example, Shields et al. (J Biol Chem 9(2), 6591-6604 (2001)) showed that amino acid substitutions at positions 298, 333, and/or 334 of the Fc region (EU numbering of residues) improve ADCC. Alternatively, increased Fc receptor binding and effector function can be obtained by altering the glycosylation of an antibody. IgG1 type antibodies, the most commonly used antibodies in cancer immunotherapy, have a conserved N-linked glycosylation site at Asn 297 in each CH2 domain of the Fc region. The two complex biantennary oligosaccharides attached to Asn 297 are buried between the CH2 domains, forming extensive contacts with the polypeptide backbone, and their presence is essential for the antibody to mediate effector functions including ADCC (Lifely et al., Glycobiology 5, 813-822 (1995); Jefferis et al., Immunol Rev 163, 59-76 (1998); Wright and Morrison, Trends Biotechnol 15, 26-32 (1997)). Umaña et al. (Nat Biotechnol 17, 176-180 (1999) and U.S. Pat. No. 6,602,684 (WO 99/54342), the contents of which are hereby incorporated by reference in their entirety) showed that overexpression of $\beta(1,4)$-N-acetylglucosaminyltransferase III (GnTIII), a glycosyltransferase catalyzing the formation of bisected oligosaccharides, in Chinese hamster ovary (CHO) cells significantly increases the in vitro ADCC activity of antibodies produced in those cells. Overexpression of GnTIII in production cell lines leads to antibodies enriched in bisected oligosaccharides, which are generally also non-fucosylated and of the hybrid type. If in addition to GnTIII, mannosidase II (ManII) is overexpressed in production cell lines, antibodies enriched in bisected, non-fucosylated oligosaccharides of the complex type are obtained (Ferrara et al., Biotechn Bioeng 93, 851-861 (2006)). Both types of antibodies show strongly increased ADCC, as compared to antibodies with unmodified glycans, but only antibodies in which the majority of the N-glycans are of the complex type are able to induce significant complement-dependent cytotoxicity (Ferrara et al., Biotechn Bioeng 93, 851-861 (2006)). The elimination of fucose from the innermost N-acetylglucosamine residue of the oligosaccharide core appears to be the critical factor for the increase of ADCC activity (Shinkawa et al., J Biol Chem 278, 3466-3473 (2003)). Therefore, further methods for producing antibodies with reduced fucosylation were developed, including e.g. expression in $\alpha(1,6)$-fucosyltransferase deficient host cells (Yamane-Ohnuki et al., Biotech Bioeng 87, 614-622 (2004); Niwa et al., J Immunol Methods 306, 151-160 (2006)).

T cells are another major immune cell population which are highly effective in killing cancer cells. The contribution of T cells in fighting cancer cells has been established from several cancer indications, including colorectal cancers (CRC), non-small cell lung cancer (NSCLC) and head and neck squamous cell carcinoma (NHSCC). See for example Galon et al. 2006, Fridman et al. 2011, Halama et al. 2011, Hiraoka et al. 2006, Al-Shibli et al. 2008, Kawai et al. 2008, Welsh et al. 2005, Dieu-Nosjean et al. 2008, Brandwein-Gensler et al. 2005, Zhang et al. 2010, Badoual et al. 2006, Rajjoub et al. 2007, and Le et al. 2005.

Several ADCC-enhanced antibodies, including the glycoengineered anti-EGFR antibody imgatuzumab, as well as the glycoengineered anti-CD20 antibody obinutuzumab and a glycoengineered anti-Her3 antibody (WO 2011/076683; US20110171222) have shown promising results in clinical development. However, despite the great potential of ADCC-enhanced antibodies, in particular for cancer therapy, a diagnostic assay for selection of those patients which will most benefit from treatment with such antibodies has yet to be generated. In view of the potential adverse effects associated with ineffective cancer therapies, it is generally acknowledged that there is a need for individualizing cancer treatment.

Therefore, it is an aim of the present invention to provide methods for determining which patients respond particularly well to ADCC-enhanced antibody therapy.

SUMMARY OF THE INVENTION

Investigations of the status of biomarkers related to anti-tumor immune responses revealed that the level of tumor infiltration by CD3+ (T cells) and CD 16+ cells prior to treatment with ADCC-enhanced antibodies correlated with an improved treatment outcome in several types of cancer.

The present invention is therefore related to a method of predicting the response of a cancer patient to treatment with an ADCC-enhanced antibody, comprising determining the level of CD3+ and CD16+ cell infiltration in the tumor of the patient prior to treatment and comparing said level of CD3+ and CD16+ cell infiltration to a reference level, wherein a higher level of CD3+ and CD16+ cell infiltration compared to the reference level is indicative for a patient who will derive clinical benefit from the treatment.

In a further aspect the present invention provides an ADCC-enhanced antibody for use in the treatment of a cancer patient, wherein the patient is selected for treatment when the level of CD3+ and CD16+ cell infiltration in the tumor of the patient prior to treatment is above a reference level.

The present invention also provides an ADCC-enhanced antibody for use in the treatment of cancer in a patient, wherein i) the level of CD3+ and CD16+ cell infiltration in the tumor of the patient is determined prior to treatment, ii) the level of CD3+ and CD16+ cell infiltration is compared to a reference level, and iii) a patient having a higher level of CD3+ and CD16+ cell infiltration compared to the reference level is selected for treatment with an ADCC-enhanced antibody.

In a further aspect the present invention provides an ADCC-enhanced antibody for use in the treatment of cancer in a patient, wherein i) the level of CD3+ and CD16+ cell infiltration in the tumor of the patient is determined prior to treatment, ii) the level of CD3+ and CD16+ cell infiltration is compared to a reference level, and iii) the ADCC-enhanced antibody is administered to a patient having a higher level of CD3+ and CD16+ cell infiltration compared to the reference level.

The present invention also provides a method for the treatment of cancer in a patient, the method comprising (i) determining the level of CD3+ and CD16+ cell infiltration in the tumor of the patient prior to treatment, (ii) comparing said level of CD3+ and CD16+ cell infiltration to a reference level, and (iii) identifying the patient as more likely to respond to treatment with an ADCC-enhanced antibody when the level of CD3+ and CD16+ cell infiltration in the tumor of the patient prior to treatment is above the reference level. In one embodiment the method further comprises (iv) administering an ADCC-enhanced antibody to the patient when the level of CD3+ and CD16+ cell infiltration in the tumor of the patient prior to treatment is above the reference level.

The present invention also provides a method for the treatment of cancer in a patient, wherein i) the level of CD3+ and CD16+ cell infiltration in the tumor of the patient is determined prior to treatment, and ii) an ADCC-enhanced antibody is administered to a patient if the level of CD3+ and CD16+ cell infiltration in the tumor of the patient is higher than a reference level.

Further provided is a method of treating cancer in a patient comprising administering an effective amount of an ADCC-enhanced antibody to the patient, provided that the level of CD3+ and CD16+ cell infiltration in the tumor of the patient prior to treatment is higher than a reference level.

The present invention also relates to a pharmaceutical composition comprising an ADCC-enhanced antibody for the treatment of a cancer patient having an increased level of CD3+ and CD16+ cell infiltration in the tumor prior to treatment relative to a reference level.

In a further aspect the invention relates to a kit for detecting the level of CD3+ and CD16+ cell infiltration in a tumor, the kit comprising i) one or more compounds for detecting the level of CD3+ and CD16+ cell infiltration.

In yet another aspect the invention relates to the in vitro use of an agent that specifically binds CD3 and CD16 for identifying a cancer patient as likely to respond to a therapy comprising an ADCC-enhanced antibody, wherein the level of CD3+ and CD16+ cell infiltration in the tumor of the patient prior to treatment is determined, wherein the level of CD3+ and CD16+ cell infiltration in the tumor above a reference level identifies that the patient is likely to respond to the therapy.

In a further aspect the invention provides the use of an agent that specifically binds CD3 and CD16 for the manufacture of a diagnostics for assessing the likelihood of response of a cancer patient to a therapy comprising an ADCC-enhanced antibody, wherein the level of CD3+ and CD16+ cell infiltration in the tumor of the patient prior to treatment is determined, and wherein the level of CD3+ and CD16+ cell infiltration in the tumor prior to treatment above a reference level identifies that the patient is likely to respond to the therapy.

BRIEF DESCRIPTION OF THE FIGURES

FIG. 7 shows a schematic of the study design for phI BP22349 mode of action study in head and neck squamous cell carcinoma patients.

DETAILED DESCRIPTION OF THE INVENTION

1. Definitions

Figure 1:
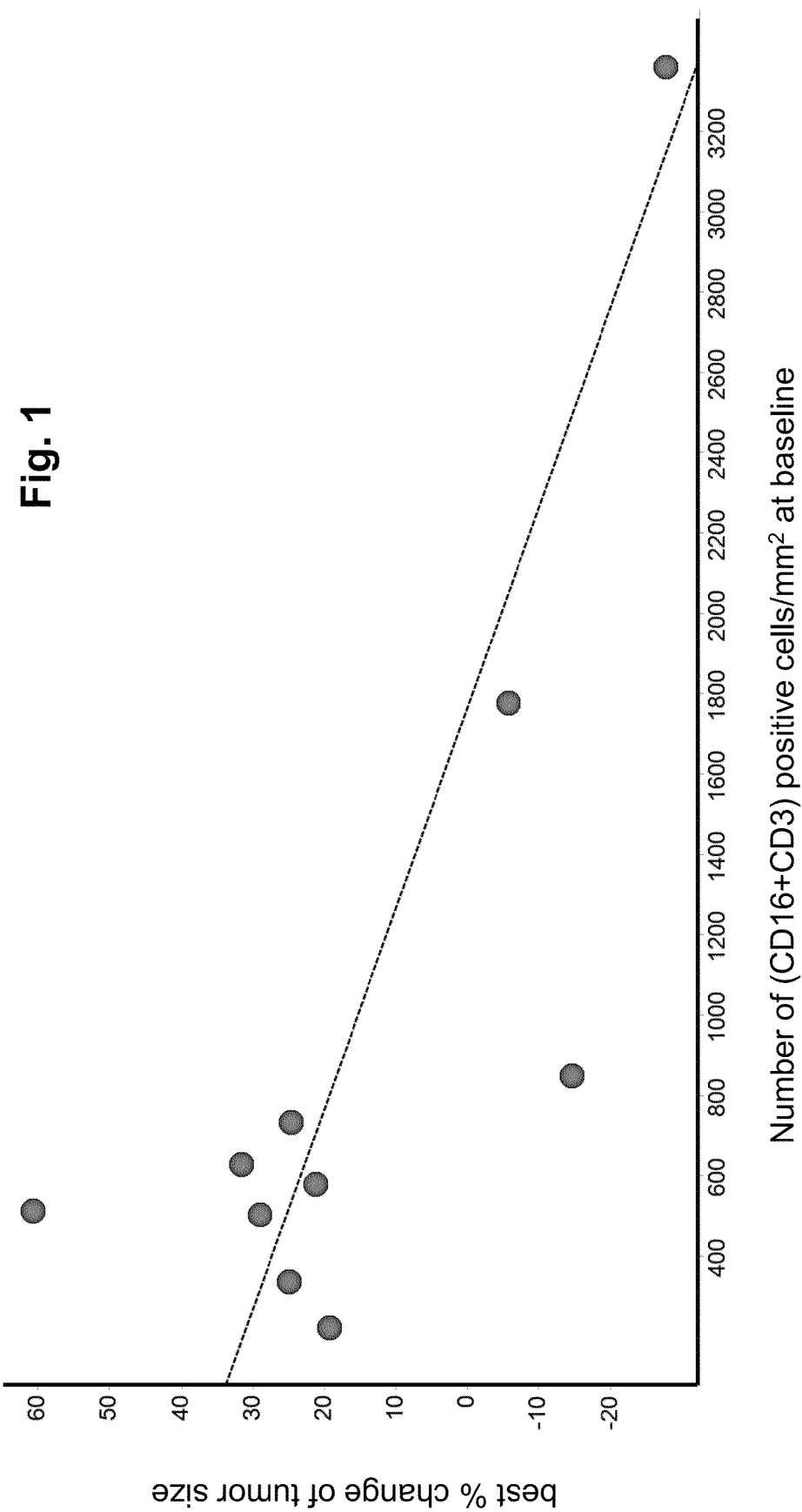
FIG. 1 (from extension cohort of phI BO21495 in KRAS mutant colorectal cancer (mCRC) patients) shows the correlation between the best percent change of the sum of longest diameter (SLD) from baseline and baseline staining in new tumour biopsies obtained at baseline for the sum of CD3+ and CD16+ cells. In all given examples the numbers of CD3+ and CD16+ cells/mm$^2$ at baseline are added up and are presented as the sum of CD3+ and CD 16+ cells. The dotted line represents the straight line fit.

The terms "administration" or "administering" as used herein mean the administration of a pharmaceutical composition, such as an ADCC-enhanced antibody, to a patient in need of such treatment or medical intervention by any suitable means known in the art. Nonlimiting routes of administration include by oral, intravenous, intraperitoneal, subcutaneous, intramuscular, topical, intradermal, intranasal or intrabronchial administration (for example as effected by inhalation). Particularly preferred in context of this invention is parenteral administration, e.g., intravenous administration.

The term "cancer" refers to the physiological condition in mammals that is typically characterized by unregulated cell proliferation. Examples of cancer include but are not limited to, carcinoma, lymphoma, blastoma, sarcoma and leukemia.

More particular examples of such cancers include squamous cell cancer, lung cancer (including small-cell lung cancer, non-small cell lung cancer, adenocarcinoma of the lung, non-squamous and squamous carcinoma of the lung), cancer of the peritoneum, hepatocellular cancer, gastric or stomach cancer (including gastrointestinal cancer), pancreatic cancer (including metastic pancreatic cancer), glioblastoma, cervical cancer, ovarian cancer, liver cancer, bladder cancer, hepatoma, breast cancer (including locally advanced, recurrent or metastatic HER-2 negative breast cancer and locally recurrent or metastatic HER2 positive breast cancer), colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome. By "tumor" as referred to herein is meant particularly the primary tumor of a patient.

The term "effective amount" refers to an amount of a drug alone or in combination with other drug or treatment regimen effective to treat a disease or disorder in a mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the drug may prevent growth and/or kill existing cancer cells, it may be cytostatic and/or cytotoxic. For cancer therapy, efficacy in vivo can, for example, be measured by assessing the duration of survival, duration of progression free survival (PFS), the response rates (RR), duration of response, and/or quality of life.

The term "overall survival (OS)" refers to the length of time during and after treatment the patient survives. As the skilled person will appreciate, a patient's overall survival is improved or enhanced, if the patient belongs to a subgroup of patients that has a statistically significant longer mean survival time as compared to another subgroup of patients.

The term "patient" refers to any single animal, more specifically a mammal (including such non-human animals as, for example, dogs, cats, horses, rabbits, zoo mammal, cows, pigs, sheep, and non-human primates) for which treatment is desired. Even more specifically, the patient herein is a human.

The term "pharmaceutical composition" refers to a sterile preparation that is in such form as to permit the biological activity of the medicament to be effective, and which contains no additional components that are unacceptably toxic to a subject to which the formulation would be administered.

The term "progression-free survival (PFS)" refers to the length of time during and after treatment during which, according to the assessment of the treating physician or investigator, or independent reviewers, the patient's disease does not become worse, i.e., does not progress. As the skilled person will appreciate, a patient's progression-free survival is improved or enhanced if the patient belongs to a subgroup of patients that has a longer length of time during which the disease does not progress as compared to the average or mean progression free survival time of a control group of similarly situated patients.

As used herein, "therapy" or "treatment" (and grammatical variations thereof such as "treat" or "treating") refers to clinical intervention in an attempt to alter the natural course of a disease in the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis.

A "value representative of the level of CD3+ and CD16+ cell infiltration in tumors of a population of patients deriving no clinical benefit from the treatment" refers to an estimate of a mean infiltration level of CD3+ and CD16+ cells in tumors of a population of patients who do not derive a clinical benefit from the treatment.

"Clinical benefit" or "response to therapy" (and grammatical versions thereof such as "respond" or "responsiveness") is defined as having an objective response (e.g. according to RECIST criteria) or disease stabilization. In certain embodiments, the disease is stabilized for at least 6, 12, 24 weeks, or longer. In some embodiments, the clinical benefit is an increase in overall survival. In some embodiments, the clinical benefit is an increase in progression-free survival. In some embodiments, the clinical benefit is a reduction in tumor size.

The CD16 antigen is a cell surface antigen expressed on certain immune cells. It exists both as a transmembrane form (CD16a, Fcγ receptor IIIa), which is expressed e.g. on natural killer (NK) cells and activated macrophages, and as a glycosylphosphatidyl-inositol (GPI)-anchored form (CD16b, FcγRIIIb) expressed on neutrophils. "CD16" as used herein refers particularly to the CD16a antigen, also known as Fcγ receptor IIIa (see UniProt accession no. P08637 [version 136] and NCBI accession no. NP_000560 [version NP_000560.5] for the human protein). Accordingly, the term "CD16 positive cells" or "CD16+ cells" refers to cells expressing the CD16 antigen, particularly the CD16a antigen. CD16+ cells are detectable in a tissue sample for example by immunohistochemistry using an anti-CD16 antibody, such as the anti-CD16 antibody clone 2H7 (available from Biogenex), which does not differentiate between FcγRIIIa and FcγRIIIb.

The CD3 antigen complex is a multimeric cell surface protein complex expressed on mature T cells. It is composed of four polypeptide chains ($\epsilon$, $\gamma$, $\delta$, $\zeta$). This complex associates with the T cell receptor (TCR). Accordingly the term "CD3 positive cell" or "CD3+ cells" refers to cells expressing the CD3 antigen. CD3+ cells are detectable in a tissue sample for example by immunohistochemistry using an anti-CD3 antibody, such as the anti-CD3 antibody clone 2GV6 (Ventana Medical Systems, Inc, Arizona).

The "level of CD3+ and CD16+ cell infiltration" refers to the number of CD3+ cells and CD16+ cells present in a given tissue, e.g. a tumor. In one embodiment, the number of CD3+ cells and CD16+ cells is determined as the mathematical sum of both markers by addition of CD3+ cell numbers plus numbers of CD16+ cells. In another embodiment, the number of CD3+ cells and CD16+ cells is determined as a combination of CD3+ and CD16+ cells, for example, by adding a multiplication factor to one of the markers or by weighting one marker heavier than the other. In a particular embodiment, the level of CD3+ and CD16+ cell infiltration is reflected by the number of CD3+ cells and CD16+ cells per mm$^2$ of a tissue section (e.g. a section prepared from a tumor biopsy for the purpose of immunohistochemical analysis). In another embodiment, the level of CD3+ and CD16+ cell infiltration is reflected by the number of CD3+ cells and CD16+ cells per total number of cells in a tissue sample (e.g. a (part of) a tumor biopsy processed for flow cytometric analysis). In yet another embodiment, the level of CD3+ and CD16+ cell infiltration is reflected by the amount of CD3 and CD16 protein or mRNA present in a tissue sample (e.g. a (part of) a tumor biopsy processed for ELISA analysis or a tissue sample processed for RT-PCT analysis). In certain embodiments, the term "above the reference level" or "higher than the reference level" refers to a level of CD3+ and CD16+ cell infiltration in the tumor sample from the individual or patient above the reference level or to an overall increase of 5%, 10%, 20%, 25%, 30%, 40%, 50%, 60%, 70%, 80%, 85%, 90%, 95%, 100% or greater, determined by the methods described herein, as compared to the reference level. In certain embodiments, the term increase refers to the increase in the level of CD3+ and CD16+ cell infiltration in the tumor sample from the individual or patient wherein, the increase is at least about 1.2-, 1.5-, 1.75-, 2-, 3-, 4-, 5-, 6-, 7-, 8-, 9-, 10-, 15-, 20-, 25-, 30-, 40-, 50-, 60-, 70-, 75-, 80-, 90-, or 100-fold higher as compared to the reference level, e.g. predetermined from a reference sample.

The term "comparing" as used herein refers to comparing the level of CD3+ and CD16+ cell infiltration in the tumor sample from the individual or patient with the reference level of the CD3+ and CD16+ cell infiltration specified elsewhere in this description. It is to be understood that comparing as used herein usually refers to a comparison of corresponding parameters or values, e.g., an absolute amount is compared to an absolute reference amount while a concentration is compared to a reference concentration or an intensity signal obtained from the biomarker in a sample is compared to the same type of intensity signal obtained from a reference sample. The comparison may be carried out manually or computer assisted. Thus, the comparison may be carried out by a computing device (e.g., of a system disclosed herein). The value of the measured or detected level of the biomarker in the sample from the individual or patient and the reference level can be, e.g., compared to each other and the said comparison can be automatically carried out by a computer program executing an algorithm for the comparison. The computer program carrying out the said evaluation will provide the desired assessment in a suitable output format. For a computer assisted comparison, the value of the determined amount may be compared to values corresponding to suitable references which are stored in a database by a computer program. The computer program may further evaluate the result of the comparison, i.e. automatically provide the desired assessment in a suitable output format. For a computer assisted comparison, the value of the determined amount may be compared to values corresponding to suitable references which are stored in a database by a computer program. The computer program may further evaluate the result of the comparison, i.e. automatically provides the desired assessment in a suitable output format.

By "prior to treatment" is meant before the first administration of ADCC-enhanced antibody to the patient.

The term "sample" refers to a sample of a body fluid, to a sample of separated cells or to a sample from a tissue or an organ. Samples of body fluids can be obtained by well-known techniques and include, samples of blood, plasma, serum, urine, lymphatic fluid, sputum, ascites, bronchial lavage or any other bodily secretion or derivative thereof. Tissue or organ samples may be obtained from any tissue or organ by, e.g., biopsy. Separated cells may be obtained from the body fluids or the tissues or organs by separating techniques such as centrifugation or cell sorting. E.g., cell-, tissue- or organ samples may be obtained from those cells, tissues or organs which express or produce the biomarker. The sample may be frozen, fresh, fixed (e.g. formalin fixed), centrifuged, and/or embedded (e.g. paraffin embedded), etc. The cell sample can, of course, be subjected to a variety of well-known post-collection preparative and storage techniques (e.g., nucleic acid and/or protein extraction, fixation, storage, freezing, ultrafiltration, concentration, evaporation, centrifugation, etc.) prior to assessing the amount of the marker in the sample. Likewise, biopsies may also be subjected to post-collection preparative and storage techniques, e.g., fixation.

In certain embodiments, the term "reference level" herein refers to a predetermined value. In this context "level" encompasses the absolute amount, the relative amount or concentration as well as any value or parameter which correlates thereto or can be derived therefrom. As the skilled artisan will appreciate the reference level is predetermined and set to meet routine requirements in terms of e.g. specificity and/or sensitivity. These requirements can vary, e.g. from regulatory body to regulatory body. It may for example be that assay sensitivity or specificity, respectively, has to be set to certain limits, e.g. 80%, 90%, 95% or 98%, respectively. These requirements may also be defined in terms of positive or negative predictive values. Nonetheless, based on the teaching given in the present invention it will always be possible for a skilled artisan to arrive at the reference level meeting those requirements. In one embodiment the reference level is determined in reference samples from individuals deriving no clinical benefit from the treatment. The reference level in one embodiment has been predetermined in reference samples from the disease entity to which the patient belongs. In certain embodiments the reference level can e.g. be set to any percentage between 25% and 75% of the overall distribution of the values in a disease entity investigated. In other embodiments the reference level can e.g. be set to the median, tertiles or quartiles as determined from the overall distribution of the values in reference samples from a disease entity investigated. In one embodiment the reference level is set to the median value as determined from the overall distribution of the values in a disease entity investigated. The reference level may vary depending on various physiological parameters such as age, gender or subpopulation, as well as on the means used for the determination of the biomarker Y referred to herein. In one embodiment, the reference sample is from essentially the same type of cells, tissue, organ or body fluid source as the sample from the individual or patient subjected to the method of the invention, e.g. if according to the invention a tumor biopsy is used as a sample to determine the level of CD3+ and CD16+ cell infiltration in the individual, the reference level is also determined in a tumor biopsy or a part thereof.

Imgatuzumab" refers to a glycoengineered, humanized IgG1-subclass anti-human EGFR antibody (CAS Registry Number 959963-46-3) based on the rat ICR62 antibody (Modjtahedi et al. (1996), Br J Cancer 73, 228-235). The antibody is produced in host cells overexpressing polypeptides having β(1,4)-N-acetylglucosaminyltransferase III (GnTIII) and mannosidase II (ManII) activity (see Umaña et al. (1999) Nat Biotechnol 17, 176-180 and U.S. Pat. No. 6,602,684 (WO 99/54342), Ferrara et al. (2006) Biotechn Bioeng 93, 851-861) and has an increased percentage of non-fucosylated oligosaccharides in its Fc region, as compared to a corresponding non-glycoengineered antibody.

The term "antibody" herein is used in the broadest sense and encompasses various antibody structures, including but not limited to monoclonal antibodies, polyclonal antibodies, multispecific antibodies (e.g. bispecific antibodies), and antibody fragments so long as they exhibit the desired antigen-binding activity and comprise an Fc region or a region equivalent to the Fc region of an immunoglobulin.

The terms "full-length antibody", "intact antibody", and "whole antibody" are used herein interchangeably to refer to an antibody having a structure substantially similar to a native antibody structure or having heavy chains that contain an Fc region as defined herein.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3), also called a heavy chain constant region. Similarly, from N- to C-terminus, each light chain has a variable region (VL), also called a variable light domain or a light chain variable domain, followed by a constant light (CL) domain, also called a light chain constant region. The light chain of an antibody may be assigned to one of two types, called kappa (κ) and lambda (λ) based on the amino acid sequence of its constant domain.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')₂, diabodies, linear antibodies, single-chain antibody molecules (e.g. scFv), single-domain antibodies, and multispecific antibodies formed from antibody fragments. For a review of certain antibody fragments, see Hudson et al., Nat Med 9, 129-134 (2003). For a review of scFv fragments, see e.g. Plückthun, in The Pharmacology of Monoclonal Antibodies, vol. 113, Rosenburg and Moore eds., Springer-Verlag, New York, pp. 269-315 (1994); see also WO 93/16185; and U.S. Pat. Nos. 5,571,894 and 5,587,458. For discussion of Fab and F(ab')₂ fragments comprising salvage receptor binding epitope residues and having increased in vivo half-life, see U.S. Pat. No. 5,869,046. Diabodies are antibody fragments with two antigen-binding sites that may be bivalent or bispecific. See, for example, EP 404,097; WO 1993/01161; Hudson et al., Nat Med 9, 129-134 (2003); and Hollinger et al., Proc Natl Acad Sci USA 90, 6444-6448 (1993). Triabodies and tetrabodies are also described in Hudson et al., Nat Med 9, 129-134 (2003). Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see e.g. U.S. Pat. No. 6,248,516 B1). Antibody fragments can be made by various techniques, including but not limited to proteolytic digestion of an intact antibody as well as production by recombinant host cells (e.g. E. coli or phage), as described herein.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). See, e.g., Kindt et al., Kuby Immunology, 6th ed., W.H. Freeman and Co., page 91 (2007). A single VH or VL domain may be sufficient to confer antigen-binding specificity.

The term "hypervariable region" or "HVR", as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the complementarity determining regions (CDRs), the latter being of highest sequence variability and/or involved in antigen recognition. With the exception of CDR1 in VH, CDRs generally comprise the amino acid residues that form the hypervariable loops. Hypervariable regions (HVRs) are also referred to as "complementarity determining regions" (CDRs), and these terms are used herein interchangeably in reference to portions of the variable region that form the antigen binding regions. This particular region has been described by Kabat et al., U.S. Dept. of Health and Human Services, Sequences of Proteins of Immunological Interest (1983) and by Chothia et al., J Mol Biol 196:901-917 (1987), where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth below in Table 1 as a comparison. The exact residue numbers which encompass a particular CDR will vary depending on the sequence and size of the CDR. Those skilled in the art can routinely determine which residues comprise a particular CDR given the variable region amino acid sequence of the antibody.

TABLE 1

CDR Definitions[1]

| CDR | Kabat | Chothia | AbM[2] |
|---|---|---|---|
| $V_H$CDR1 | 31-35 | 26-32 | 26-35 |
| $V_H$CDR2 | 50-65 | 52-58 | 50-58 |
| $V_H$CDR3 | 95-102 | 95-102 | 95-102 |
| $V_L$CDR1 | 24-34 | 26-32 | 24-34 |
| $V_L$CDR2 | 50-56 | 50-52 | 50-56 |
| $V_L$CDR3 | 89-97 | 91-96 | 89-97 |

[1]Numbering of all CDR definitions in Table 1 is according to the numbering conventions set forth by Kabat et al. (see below).
[2]"AbM" with a lowercase "b" as used in Table 1 refers to the CDRs as defined by Oxford Molecular's "AbM" antibody modeling software.

Kabat et al. also defined a numbering system for variable region sequences that is applicable to any antibody. One of ordinary skill in the art can unambiguously assign this system of "Kabat numbering" to any variable region sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless otherwise specified, references to the numbering of specific amino acid residue positions in an antibody variable region are according to the Kabat numbering system.

The polypeptide sequences of the sequence listing (i.e., SEQ ID NOs 1-9.) are not numbered according to the Kabat numbering system. However, it is well within the ordinary skill of one in the art to convert the numbering of the sequences of the Sequence Listing to Kabat numbering.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called $\alpha$, $\delta$, $\epsilon$, $\gamma$, and $\mu$, respectively.

The term "Fc region" herein is used to define a C-terminal region of an immunoglobulin heavy chain that contains at least a portion of the constant region. The term includes native sequence Fc regions and variant Fc regions. Although the boundaries of the Fc region of an IgG heavy chain might vary slightly, the human IgG heavy chain Fc region is usually defined to extend from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md., 1991.

A "region equivalent to the Fc region of an immunoglobulin" is intended to include naturally occurring allelic variants of the Fc region of an immunoglobulin as well as variants having alterations which produce substitutions, additions, or deletions but which do not decrease substantially the ability of the immunoglobulin to mediate effector functions (such as antibody-dependent cell-mediated cytotoxicity). For example, one or more amino acids can be deleted from the N-terminus or C-terminus of the Fc region of an immunoglobulin without substantial loss of biological function. Such variants can be selected according to general rules known in the art so as to have minimal effect on activity (see, e.g., Bowie et al., Science 247, 1306-10 (1990)).

The terms "anti-[antigen] antibody" and "an antibody that binds to [antigen]" refer to an antibody that is capable of binding the respective antigen with sufficient affinity such that the antibody is useful as a diagnostic and/or therapeutic agent in targeting the antigen. In one embodiment, the extent of binding of an anti-[antigen] antibody to an unrelated protein is less than about 10% of the binding of the antibody to the antigen as measured, e.g., by a radioimmunoassay (RIA). In certain embodiments, an antibody that binds to [antigen] has a dissociation constant ($K_D$) of $\leq 1$ μM, $\leq 100$ nM, $\leq 10$ nM, $\leq 1$ nM, $\leq 0.1$ nM, $\leq 0.01$ nM, or $\leq 0.001$ nM (e.g. $10^{-8}$ M or less, e.g. from $10^{-8}$ M to $10^{-13}$ M, e.g., from $10^{-9}$ M to $10^{-13}$ M).

As used herein, the terms "engineer, engineered, engineering" are considered to include any manipulation of the peptide backbone or the post-translational modifications of a naturally occurring or recombinant polypeptide or fragment thereof. Engineering includes modifications of the amino acid sequence, of the glycosylation pattern, or of the side chain group of individual amino acids, as well as combinations of these approaches. "Engineering", particularly with the prefix "glyco-", as well as the term "glycosylation engineering" includes metabolic engineering of the glycosylation machinery of a cell, including genetic manipulations of the oligosaccharide synthesis pathways to achieve altered glycosylation of glycoproteins expressed in cells. Furthermore, glycosylation engineering includes the effects of mutations and cell environment on glycosylation. In one embodiment, the glycosylation engineering is an alteration in glycosyltransferase activity. In a particular embodiment, the engineering results in altered glucosaminyltransferase activity and/or fucosyltransferase activity. Glycosylation engineering can be used to obtain a "host cell having increased GnTIII activity" (e.g. a host cell that has been manipulated to express increased levels of one or more polypeptides having β(1,4)-N-acetylglucosaminyltransferase III (GnTIII) activity), a "host cell having increased ManII activity" (e.g. a host cell that has been manipulated to express increased levels of one or more polypeptides having α-mannosidase II (ManII) activity), or a "host cell having decreased α(1,6) fucosyltransferase activity" (e.g. a host cell that has been manipulated to express decreased levels of α(1,6) fucosyltransferase). A host cell is any type of cellular system that can be used to generate ADCC-enhanced antibodies. Host cells include cultured cells, e.g. mammalian cultured cells, such as CHO cells, BHK cells, NS0 cells, SP2/0 cells, YO myeloma cells, P3X63 mouse myeloma cells, PER cells, PER.C6 cells or hybridoma cells, yeast cells, insect cells, and plant cells, to name only a few, but also cells comprised within a transgenic animal, transgenic plant or cultured plant or animal tissue.

The host cells which contain the coding sequence of an antibody useful in the context the invention and/or the coding sequence of polypeptides having glycosyltransferase activity, and which express the biologically active gene products may be identified e.g. by DNA-DNA or DNA-RNA hybridization; the presence or absence of "marker" gene functions; assessing the level of transcription as measured by the expression of the respective mRNA transcripts in the host cell; or detection of the gene product as measured by immunoassay or by its biological activity—methods which are well known in the art. GnTIII or Man II activity can be detected e.g. by employing a lectin which binds to biosynthesis products of GnTIII or ManII, respectively. An example for such a lectin is the $E_4$-PHA lectin which binds preferentially to oligosaccharides containing bisecting GlcNAc. Biosynthesis products (i.e. specific oligosaccharide structures) of polypeptides having GnTIII or ManII activity can also be detected by mass spectrometric analysis of oligosaccharides released from glycoproteins produced by cells expressing said polypeptides. Alternatively, a functional assay which measures the increased effector function, e.g. increased ADCC, mediated by antibodies produced by the cells engineered with the polypeptide having GnTIII or ManII activity may be used.

As used herein, the term "polypeptide having GnTIII activity" refers to polypeptides that are able to catalyze the addition of a N-acetylglucosamine (GlcNAc) residue in β-1,4 linkage to the β-linked mannoside of the trimannosyl core of N-linked oligosaccharides. This includes fusion polypeptides exhibiting enzymatic activity similar to, but not necessarily identical to, an activity of β(1,4)-N-acetylglucosaminyltransferase III, also known as β-1,4-mannosyl-glycoprotein 4-beta-N-acetylglucosaminyl-transferase (EC 2.4.1.144), according to the Nomenclature Committee of the International Union of Biochemistry and Molecular Biology (NC-IUBMB), as measured in a particular biological assay, with or without dose dependency. In the case where dose dependency does exist, it need not be identical to that of GnTIII, but rather substantially similar to the dose-dependency in a given activity as compared to the GnTIII (i.e. the candidate polypeptide will exhibit greater activity or not more than about 25-fold less and, preferably, not more than about ten-fold less activity, and most preferably, not more than about three-fold less activity relative to the GnTIII). In certain embodiments the polypeptide having GnTIII activity is a fusion polypeptide comprising the catalytic domain of GnTIII and the Golgi localization domain of a heterologous Golgi resident polypeptide. Particularly, the Golgi localization domain is the localization domain of mannosidase II or GnTI, most particularly the localization domain of mannosidase II. Alternatively, the Golgi localization domain is selected from the group consisting of: the localization domain of mannosidase I, the localization domain of GnTII, and the localization domain of α1,6 core fucosyltransferase. Methods for generating such fusion polypeptides and using them to produce antibodies with increased effector functions are disclosed in WO2004/065540, U.S. Provisional Pat. Appl. No. 60/495,142 and U.S. Pat. Appl. Publ. No. 2004/0241817, the entire contents of which are expressly incorporated herein by reference.

As used herein, the term "Golgi localization domain" refers to the amino acid sequence of a Golgi resident polypeptide which is responsible for anchoring the polypeptide to a location within the Golgi complex. Generally, localization domains comprise amino terminal "tails" of an enzyme.

As used herein, the term "polypeptide having ManII activity" refers to polypeptides that are able to catalyze the hydrolysis of the terminal 1,3- and 1,6-linked α-D-mannose residues in the branched $GlcNAcMan_5GlcNAc_2$ mannose intermediate of N-linked oligosaccharides. This includes polypeptides exhibiting enzymatic activity similar to, but not necessarily identical to, an activity of Golgi α-mannosidase II, also known as mannosyl oligosaccharide 1,3-1,6-α-mannosidase II (EC 3.2.1.114), according to the Nomenclature Committee of the International Union of Biochemistry and Molecular Biology (NC-IUBMB).

Antibody-dependent cellular cytotoxicity (ADCC) is an immune mechanism leading to the lysis of antibody-coated target cells by immune effector cells. The target cells are cells to which antibodies or fragments thereof comprising an Fc region specifically bind, generally via the protein part that is N-terminal to the Fc region. As used herein, the term "increased ADCC" or "enhanced ADCC" is defined as either an increase in the number of target cells that are lysed in a given time, at a given concentration of antibody in the medium surrounding the target cells, by the mechanism of ADCC defined above, and/or a reduction in the concentration of antibody, in the medium surrounding the target cells, required to achieve the lysis of a given number of target cells in a given time, by the mechanism of ADCC. The increase in ADCC is relative to the ADCC mediated by the same antibody produced by the same type of host cells, using the same standard production, purification, formulation and storage methods (which are known to those skilled in the art), but that has not been engineered. For example the increase in ADCC mediated by an antibody produced by host cells engineered to have an altered pattern of glycosylation (e.g. to express the glycosyltransferase, GnTIII, or other glycosyltransferases) by the methods described herein, is relative to the ADCC mediated by the same antibody produced by the same type of non-engineered host cells.

By "antibody having increased antibody dependent cellular cytotoxicity (ADCC)" is meant an antibody having increased ADCC as determined by any suitable method known to those of ordinary skill in the art. One accepted in vitro ADCC assay is as follows:

1) the assay uses target cells that are known to express the target antigen recognized by the antigen-binding region of the antibody;

2) the assay uses human peripheral blood mononuclear cells (PBMCs), isolated from blood of a randomly chosen healthy donor, as effector cells;

3) the assay is carried out according to following protocol:
  i) the PBMCs are isolated using standard density centrifugation procedures and are suspended at $5 \times 10^6$ cells/ml in RPMI cell culture medium;
  ii) the target cells are grown by standard tissue culture methods, harvested from the exponential growth phase with a viability higher than 90%, washed in RPMI cell culture medium, labeled with 100 micro-Curies of $^{51}$Cr, washed twice with cell culture medium, and resuspended in cell culture medium at a density of $10^5$ cells/ml;
  iii) 100 microliters of the final target cell suspension above are transferred to each well of a 96-well microtiter plate;
  iv) the antibody is serially-diluted from 4000 ng/ml to 0.04 ng/ml in cell culture medium and 50 microliters of the resulting antibody solutions are added to the target cells in the 96-well microtiter plate, testing in triplicate various antibody concentrations covering the whole concentration range above;
  v) for the maximum release (MR) controls, 3 additional wells in the plate containing the labeled target cells, receive 50 microliters of a 2% (V/V) aqueous solution of non-ionic detergent (Nonidet, Sigma, St. Louis), instead of the antibody solution (point iv above);
  vi) for the spontaneous release (SR) controls, 3 additional wells in the plate containing the labeled target cells, receive 50 microliters of RPMI cell culture medium instead of the antibody solution (point iv above);
  vii) the 96-well microtiter plate is then centrifuged at 50×g for 1 minute and incubated for 1 hour at 4° C.;
  viii) 50 microliters of the PBMC suspension (point i above) are added to each well to yield an effector:target cell ratio of 25:1 and the plates are placed in an incubator under 5% $CO_2$ atmosphere at 37° C. for 4 hours;
  ix) the cell-free supernatant from each well is harvested and the experimentally released radioactivity (ER) is quantified using a gamma counter;
  x) the percentage of specific lysis is calculated for each antibody concentration according to the formula (ER−MR)/(MR−SR)×100, where ER is the average radioactivity quantified (see point ix above) for that antibody concentration, MR is the average radioactivity quantified (see point ix above) for the MR controls (see point v above), and SR is the average radioactivity quantified (see point ix above) for the SR controls (see point vi above);

4) "increased ADCC" is defined as either an increase in the maximum percentage of specific lysis observed within the antibody concentration range tested above, and/or a reduction in the concentration of antibody required to achieve one half of the maximum percentage of specific lysis observed within the antibody concentration range tested above. The increase in ADCC is relative to the ADCC, measured with the above assay, mediated by the same antibody, produced by the same type of host cells, using the same standard production, purification, formulation and storage methods, which are known to those skilled in the art, but that has not been engineered.

Other examples of in vitro assays to assess ADCC activity of an antibody are described in U.S. Pat. No. 5,500,362; Hellstrom et al. Proc Natl Acad Sci USA 83, 7059-7063 (1986) and Hellstrom et al., Proc Natl Acad Sci USA 82, 1499-1502 (1985); U.S. Pat. No. 5,821,337; Bruggemann et al., J Exp Med 166, 1351-1361 (1987). Alternatively, non-radioactive assays methods may be employed (see, for example, ACTI™ non-radioactive cytotoxicity assay for flow cytometry (CellTechnology, Inc. Mountain View, Calif.); and CytoTox 96® non-radioactive cytotoxicity assay (Promega, Madison, Wis.)). Useful effector cells for such assays include peripheral blood mononuclear cells (PBMC) and Natural Killer (NK) cells. Alternatively, or additionally, ADCC activity of the antibody may be assessed in vivo, e.g. in an animal model such as that disclosed in Clynes et al., Proc Natl Acad Sci USA 95, 652-656 (1998).

2. Detailed Embodiments

The present invention is directed, in general, to a method of predicting the response of a cancer patient to treatment with an ADCC-enhanced antibody, comprising determining the level of CD3+ and CD16+ cell infiltration in the tumor. Determining the level of both types of immune cells, CD3+ cells and CD16+ cells, provides a robust diagnostic predictive of response of a cancer patient to treatment with an ADCC-enhanced antibody. The inclusion of both CD3+ cells and CD16+ cells in the method allows for assessment of the presence of immune cell infiltration from multiple components of the immune system, each contributing to the anti-tumor effect. Additionally, presence of both markers in the tumor is strongly inter-dependent. Assessment of the level of both markers also increases the robustness of the method and allows for more accurate prediction of response to treatment with an ADCC-enhanced antibody even in situations where the tumor sample to be analysed is of limited quantity.

Accordingly, in a first aspect, the present invention provides a method of predicting the response of a cancer patient to treatment with an ADCC-enhanced antibody, comprising determining the level of CD3+ and CD16+ cell infiltration in the tumor of the patient prior to treatment and comparing said level of CD3+ and CD16+ cell infiltration to a reference level, wherein a higher level of CD3+ and CD16+ cell infiltration compared to the reference level is indicative for a patient who will derive clinical benefit from the treatment. In one embodiment, the method further comprises selecting a treatment comprising an ADCC-enhanced antibody.

In certain embodiments, the method is an in vitro method. In one such embodiment, the level of CD3+ and CD16+ cell infiltration is determined in a tumor sample taken from the patient prior to treatment. In one embodiment, the reference level is a value representative of the level of CD3+ and CD16+ cell infiltration in tumors prior to treatment of a population of patients deriving no clinical benefit from the treatment. The reference level is representative of the level of CD3+ and CD16+ cell infiltration in tumors prior to treatment below which no clinical benefit would be expected.

In one embodiment, the reference level is determined in vitro in tumor samples taken prior to treatment from patients deriving no clinical benefit from the treatment. In one embodiment, clinical benefit from the treatment with an ADCC-enhanced antibody is attributable to the ADCC activity of the antibody. In one embodiment, the level of CD3+ and CD16+ cell infiltration which is indicative for a patient who will derive clinical benefit from the treatment is at least 1.2-fold, at least 1.5-fold, at least 2-fold or at least 3-fold higher than the reference level.

In one embodiment, the level of CD3+ and CD16+ cell infiltration in the tumor of the patient prior to treatment is considered indicative for a patient who will derive clinical benefit from the treatment wherein the level of CD3+ and CD16+ cell infiltration in the tumor of the patient is at the $20^{th}$ percentile or higher, $25^{th}$ percentile or higher, $30^{th}$ percentile or higher, $35^{th}$ percentile or higher, $40^{th}$ percentile or higher, $45^{th}$ percentile or higher, $50^{th}$ percentile or higher, $55^{th}$ percentile or higher, 60th percentile or higher, $65^{th}$ percentile or higher, 70th percentile or higher, 75th percentile or higher, 80th percentile or higher, 85th percentile or higher, or 90th percentile or higher, in a population of patients with tumors of the same cancer type.

In another aspect, the present invention provides a method of predicting the response of a cancer patient to treatment with an ADCC-enhanced antibody, comprising determining the level of CD3+ and CD16+ cell infiltration in the tumor of the patient prior to treatment and comparing said level of CD3+ and CD16+ cell infiltration to a predetermined threshold CD3+ and CD16+ cell infiltration, wherein a level of CD3+ and CD16+ cell infiltration in the tumor that is higher than the predetermined threshold CD3+ and CD16+ cell infiltration level is indicative for a patient who is likely to derive clinical benefit from the treatment. In one embodiment, the method further comprises selecting a treatment comprising an ACDD-enhanced antibody. The threshold CD3+ and CD16+ cell infiltration level is determined, in one embodiment, based on a statistical analysis of CD3+ and CD16+ cell infiltration levels in tumor samples taken prior to treatment from patients who exhibit no significant clinical benefit from the treatment and distinguishes these patients from those patients who are likely to derive clinical benefit from treatment with an ADCC-enhanced antibody. In one embodiment, clinical benefit from the treatment with an ADCC-enhanced antibody is attributable to the ADCC activity of the antibody.

In one embodiment, the threshold CD3+ and CD16+ cell infiltration level is determined by quantification of CD3+ and CD16+ cells using immunohistochemistry and microscopy techniques. One example of such an assay is described in Example 1. In this assay, CD3+ and CD16+ cells are labelled and counted in fields of view under a light microscope having a grid in the eyepiece. In one embodiment, the threshold CD3+ and CD16+ cell infiltration level is about 100 cells/mm$^2$, 150 cells/mm$^2$, 200 cells/mm$^2$, about 250 cells/mm$^2$, about 300 cells/mm$^2$, about 350 cells/mm$^2$, about 400 cells/mm$^2$, about 450 cells/mm$^2$, about 500 cells/mm$^2$, about 600 cells/mm$^2$, about 700 cells/mm$^2$, about 800 cells/mm$^2$, or higher. In one embodiment, the cancer to be treated is colorectal cancer (CRC). In one embodiment, the cancer to be treated is KRAS mutant colorectal cancer (mCRC). In one embodiment, the cancer to be treated is non-squamous non-small cell lung cancer. In another embodiment, the cancer to be treated is head and neck squamous cell carcinoma.

In a further aspect the present invention provides an ADCC-enhanced antibody for use in the treatment of a cancer patient, wherein the patient is selected for treatment when the level of CD3+ and CD16+ cell infiltration in the tumor of the patient prior to treatment is above a reference level. The present invention also provides an ADCC-enhanced antibody for use in the treatment of cancer in a patient, wherein i) the level of CD3+ and CD16+ cell infiltration in the tumor of the patient is determined prior to treatment, ii) the level of CD3+ and CD16+ cell infiltration is compared to a reference level, and iii) a patient having a higher level of CD3+ and CD16+ cell infiltration compared to the reference level is selected for treatment with an ADCC-enhanced antibody. The present invention further provides an ADCC-enhanced antibody for use in the treatment of cancer in a patient, wherein i) the level of CD3+ and CD16+ cell infiltration in the tumor of the patient is determined prior to treatment, ii) the level of CD3+ and CD16+ cell infiltration is compared to a reference level, and iii) the ADCC-enhanced antibody is administered to a patient having a higher level of CD3+ and CD16+ cell infiltration compared to the reference level. The reference level is representative of the level of CD3+ and CD16+ cell infiltration in tumors prior to treatment below which no clinical benefit would be expected.

In one embodiment, the level of CD3+ and CD16+ cell infiltration in the tumor is determined in vitro in a tumor sample taken from the patient prior to treatment. In one embodiment, the reference level is a value representative of the level of CD3+ and CD16+ cell infiltration in tumors prior to treatment of a population of patients deriving no clinical benefit from the treatment. In one embodiment, the reference level is determined in vitro in tumor samples taken prior to treatment from patients deriving no clinical benefit from the treatment. In one embodiment, clinical benefit from the treatment with an ADCC-enhanced antibody is attributable to the ADCC activity of the antibody. In one embodiment, the ADCC-enhanced antibody is administered to a patient having an at least 1.2-fold, at least 1.5-fold, at least 2-fold or at least 3-fold higher level of CD3+ and CD 16+ cell infiltration compared to the reference level.

In one embodiment, the level of CD3+ and CD16+ cell infiltration in the tumor of the patient prior to treatment is considered indicative for a patient who will derive clinical benefit from the treatment wherein the level of CD3+ and CD16+ cell infiltration in the tumor of the patient is at the $20^{th}$ percentile or higher, $25^{th}$ percentile or higher, $30^{th}$ percentile or higher, $35^{th}$ percentile or higher, $40^{th}$ percentile or higher, $45^{th}$ percentile or higher, $50^{th}$ percentile or higher, $55^{th}$ percentile or higher, 60th percentile or higher, $65^{th}$ percentile or higher, 70th percentile or higher, 75th percentile or higher, 80th percentile or higher, 85th percentile or higher, or 90th percentile or higher, in a population of patients with tumors of the same cancer type.

In another aspect the present invention provides an ADCC-enhanced antibody for use in the treatment of a cancer patient, wherein the patient is selected for treatment when the level of CD3+ and CD16+ cell infiltration in the tumor of the patient prior to treatment is above a threshold level. The present invention also provides an ADCC-enhanced antibody for use in the treatment of cancer in a patient, wherein i) the level of CD3+ and CD16+ cell infiltration in the tumor of the patient is determined prior to treatment, ii) the level of CD3+ and CD16+ cell infiltration is compared to a threshold level, and iii) a patient having a higher level of CD3+ and CD16+ cell infiltration compared to the threshold level is selected for treatment with an ADCC-enhanced antibody. The present invention further provides an ADCC-enhanced antibody for use in the treatment of cancer in a patient, wherein i) the level of CD3+ and CD16+ cell infiltration in the tumor of the patient is determined prior to treatment, ii) said level of CD3+ and CD16+ cell infiltration is compared to a threshold CD3+ and CD16+ cell infiltration level, and iii) the ADCC-enhanced antibody is administered to a patient having a higher level of CD3+ and CD16+ cell infiltration than a threshold CD3+ and CD16+ cell infiltration level. In one embodiment, the threshold CD3+ and CD16+ cell infiltration level is about 100 cells/mm$^2$, 150 cells/mm$^2$, 200 cells/mm$^2$, about 250 cells/mm$^2$, about 300 cells/mm$^2$, about 350 cells/mm$^2$, about 400 cells/mm$^2$, about 450 cells/mm$^2$, about 500 cells/mm$^2$, about 600 cells/mm$^2$, about 700 cells/mm$^2$, about 800 cells/mm$^2$, or higher. In one embodiment, the cancer to be treated is colorectal cancer (CRC). In one embodiment, the cancer to be treated is KRAS mutant colorectal cancer (mCRC). In one embodiment, the cancer to be treated is non-squamous non-small cell lung cancer. In another embodiment, the cancer to be treated is head and neck squamous cell carcinoma.

The present invention also provides a method for the treatment of cancer in a patient, the method comprising (i) determining the level of CD3+ and CD16+ cell infiltration in the tumor of the patient prior to treatment, (ii) comparing said level of CD3+ and CD16+ cell infiltration to a reference level, and (iii) identifying the patient as more likely to respond to treatment with an ADCC-enhanced antibody when the level of CD3+ and CD16+ cell infiltration in the tumor of the patient prior to treatment is above the reference level. In one embodiment the method further comprises (iv) administering an ADCC-enhanced antibody to the patient when the level of CD3+ and CD16+ cell infiltration in the tumor of the patient prior to treatment is above the reference level. The present invention also provides a method for the treatment of cancer in a patient, wherein i) the level of CD3+ and CD16+ cell infiltration in the tumor of the patient is determined prior to treatment, and ii) an ADCC-enhanced antibody is administered to a patient if the level of CD3+ and CD16+ cell infiltration in the tumor of the patient is higher than a reference level.

In one embodiment, the level of CD3+ and CD16+ cell infiltration in the tumor is determined in vitro in a tumor sample taken from the patient prior to treatment. In one embodiment, the reference level is a value representative of the level of CD3+ and CD16+ cell infiltration in tumors prior to treatment of a population of patients deriving no clinical benefit from the treatment. The reference level is representative of the level of CD3+ and CD16+ cell infiltration in tumors prior to treatment below which no clinical benefit would be expected.

In one embodiment, the reference level is determined in vitro in tumor samples taken prior to treatment from patients deriving no clinical benefit from the treatment. In one embodiment, clinical benefit from the treatment with an ADCC-enhanced antibody is attributable to the ADCC activity of the antibody. In one embodiment, the ADCC-enhanced antibody is administered to a patient having an at least 1.2-fold, at least 1.5-fold, at least 2-fold or at least 3-fold higher level of CD3+ and CD16+ cell infiltration compared to the reference level.

In one embodiment, the level of CD3+ and CD16+ cell infiltration in the tumor of the patient prior to treatment is considered indicative for a patient who will derive clinical benefit from the treatment wherein the level of CD3+ and CD16+ cell infiltration in the tumor of the patient is at the $20^{th}$ percentile or higher, $25^{th}$ percentile or higher, $30^{th}$ percentile or higher, $35^{th}$ percentile or higher, $40^{th}$ percentile or higher, $45^{th}$ percentile or higher, $50^{th}$ percentile or higher, $55^{th}$ percentile or higher, 60th percentile or higher, $65^{th}$ percentile or higher, 70th percentile or higher, 75th percentile or higher, 80th percentile or higher, 85th percentile or higher, or 90th percentile or higher, in a population of patients with tumors of the same cancer type.

The present invention further provides a method for the treatment of cancer in a patient, the method comprising (i) determining the level of CD3+ and CD16+ cell infiltration in the tumor of the patient prior to treatment, (ii) comparing said level of CD3+ and CD16+ cell infiltration to a threshold level, and (iii) identifying the patient as more likely to respond to treatment with an ADCC-enhanced antibody when the level of CD3+ and CD16+ cell infiltration in the tumor of the patient prior to treatment is above the threshold level. In one embodiment the method further comprises (iv) administering an ADCC-enhanced antibody to the patient when the level of CD3+ and CD16+ cell infiltration in the tumor of the patient prior to treatment is above the threshold level. The present invention also provides a method for the treatment of cancer in a patient, wherein i) the level of CD3+ and CD16+ cell infiltration in the tumor of the patient is determined prior to treatment, and ii) an ADCC-enhanced antibody is administered to the patient if the level of CD3+ and CD16+ cell infiltration in the tumor of the patient is higher than a threshold CD3+ and CD16+ cell infiltration level.

In one embodiment, the threshold CD3+ and CD16+ cell infiltration level is about 100 cells/mm$^2$, 150 cells/mm$^2$, 200 cells/mm$^2$, about 250 cells/mm$^2$, about 300 cells/mm$^2$, about 350 cells/mm$^2$, about 400 cells/mm$^2$, about 450 cells/mm$^2$, about 500 cells/mm$^2$, about 600 cells/mm$^2$, about 700 cells/mm$^2$, about 800 cells/mm$^2$, or higher. In one embodiment, the cancer to be treated is colorectal cancer (CRC). In one embodiment, the cancer to be treated is KRAS mutant colorectal cancer (mCRC). In one embodiment, the cancer to be treated is non-squamous non-small cell lung cancer. In another embodiment, the cancer to be treated is head and neck squamous cell carcinoma.

Further provided is a method of treating cancer in a patient comprising administering an effective amount of an ADCC-enhanced antibody to the patient, provided that the level of CD3+ and CD16+ cell infiltration in the tumor of the patient prior to treatment is higher than a reference level. In one embodiment, the level of CD3+ and CD16+ cell infiltration in the tumor is the level determined in vitro in a tumor sample taken from the patient prior to treatment. In one embodiment, the reference level is a value representative of the level of CD3+ and CD16+ cell infiltration in tumors prior to treatment of a population of patients deriving no clinical benefit from the treatment. The reference level is representative of the level of CD3+ and CD16+ cell infiltration in tumors prior to treatment below which no clinical benefit would be expected.

In one embodiment, the reference level is determined in vitro in tumor samples taken prior to treatment from patients deriving no clinical benefit from the treatment. In one embodiment, clinical benefit from the treatment with an ADCC-enhanced antibody is attributable to the ADCC activity of the antibody. In one embodiment, the level of CD3+ and CD16+ cell infiltration is at least 1.2-fold, at least 1.5-fold, at least 2-fold or at least 3-fold higher compared to the reference level.

In one embodiment, the level of CD3+ and CD16+ cell infiltration in the tumor of the patient prior to treatment is considered indicative for a patient who will derive clinical benefit from the treatment wherein the level of CD3+ and CD16+ cell infiltration in the tumor of the patient is at the 20$^{th}$ percentile or higher, 25$^{th}$ percentile or higher, 30$^{th}$ percentile or higher, 35$^{th}$ percentile or higher, 40$^{th}$ percentile or higher, 45$^{th}$ percentile or higher, 50$^{th}$ percentile or higher, 55$^{th}$ percentile or higher, 60th percentile or higher, 65$^{th}$ percentile or higher, 70th percentile or higher, 75th percentile or higher, 80th percentile or higher, 85th percentile or higher, or 90th percentile or higher, in a population of patients with tumors of the same cancer type.

Further provided is a method of treating cancer in a patient comprising administering an effective amount of an ADCC-enhanced antibody to the patient, provided that the level of CD3+ and CD16+ cell infiltration in the tumor of the patient prior to treatment is higher than a threshold CD3+ and CD16+ cell infiltration level. In one embodiment, the threshold CD3+ and CD16+ cell infiltration level is about 100 cells/mm$^2$, 150 cells/mm$^2$, 200 cells/mm$^2$, about 250 cells/mm$^2$, about 300 cells/mm$^2$, about 350 cells/mm$^2$, about 400 cells/mm$^2$, about 450 cells/mm$^2$, about 500 cells/mm$^2$, about 600 cells/mm$^2$, about 700 cells/mm$^2$, about 800 cells/mm$^2$, or higher. In one embodiment, the cancer to be treated is colorectal cancer (CRC). In one embodiment, the cancer to be treated is KRAS mutant colorectal cancer (mCRC). In one embodiment, the cancer to be treated is non-squamous non-small cell lung cancer. In another embodiment, the cancer to be treated is head and neck squamous cell carcinoma.

In a further aspect the invention relates to a kit for detecting the level of CD3+ and CD16+ cell infiltration in a tumor, the kit comprising i) one or more compounds for detecting the level of CD3+ and CD16+ cell infiltration. In certain embodiments, the kit further comprises ii) instructions for using said kit to predict responsiveness of a cancer patient to treatment with an ADCC-enhanced antibody, wherein a higher level of CD3+ and CD16+ cell infiltration in the tumor of the patient prior to treatment, compared to a reference value, is indicative for a patient who will derive clinical benefit from the treatment.

In certain embodiments, the kit is for in vitro use. In one such embodiment, the level of CD3+ and CD16+ cell infiltration is detected in a tumor sample taken from a cancer patient prior to treatment with an ADCC-enhanced antibody. In one embodiment, the reference level is a value representative of the level of CD3+ and CD16+ cell infiltration in tumors prior to treatment of a population of patients deriving no clinical benefit from the treatment. The reference level is representative of the level of CD3+ and CD16+ cell infiltration in tumors prior to treatment below which no clinical benefit would be expected. In one embodiment, the reference level is determined in vitro in tumor samples taken prior to treatment from patients deriving no clinical benefit from the treatment. In one embodiment, clinical benefit from the treatment with an ADCC-enhanced antibody is attributable to the ADCC activity of the antibody. In one embodiment, the level of CD3+ and CD16+ cell infiltration which is indicative for a patient who will derive clinical benefit from the treatment is at least 1.2-fold, at least 1.5-fold, at least 2-fold or at least 3-fold higher than the reference level.

In one embodiment, the level of CD3+ and CD16+ cell infiltration in the tumor of the patient prior to treatment is considered indicative for a patient who will derive clinical benefit from the treatment wherein the level of CD3+ and CD16+ cell infiltration in the tumor of the patient is at the 20$^{th}$ percentile or higher, 25$^{th}$ percentile or higher, 30$^{th}$ percentile or higher, 35$^{th}$ percentile or higher, 40$^{th}$ percentile or higher, 45$^{th}$ percentile or higher, 50$^{th}$ percentile or higher, 55$^{th}$ percentile or higher, 60th percentile or higher, 65$^{th}$ percentile or higher, 70th percentile or higher, 75th percentile or higher, 80th percentile or higher, 85th percentile or higher, or 90th percentile or higher, in a population of patients with tumors of the same cancer type.

In a further aspect the invention relates to a kit for detecting the level of CD3+ and CD16+ cell infiltration in a tumor, the kit comprising i) one or more compounds for detecting the level of CD3+ and CD16+ cell infiltration. In certain embodiments, the kit further comprises ii) instructions for using said kit to predict responsiveness of a cancer patient to treatment with an ADCC-enhanced antibody, wherein a higher level of CD3+ and CD16+ cell infiltration in the tumor of the patient prior to treatment, compared to a threshold CD3+ and CD16+ cell infiltration level, is indicative for a patient who will derive clinical benefit from the treatment. In certain embodiments, the kit is for in vitro use. In one such embodiment, the level of CD3+ and CD16+ cell infiltration is detected in a tumor sample taken from a cancer patient prior to treatment with an ADCC-enhanced antibody. In one embodiment, the threshold CD3+ and CD16+ cell infiltration level is about 100 cells/mm$^2$, 150 cells/mm$^2$, 200 cells/mm$^2$, about 250 cells/mm$^2$, about 300 cells/mm$^2$, about 350 cells/mm$^2$, about 400 cells/mm$^2$, about 450 cells/mm$^2$, about 500 cells/mm$^2$, about 600 cells/mm$^2$, about 700 cells/mm$^2$, about 800 cells/mm$^2$, or higher. In one embodiment, the cancer to be treated is colorectal cancer (CRC). In one embodiment, the cancer to be treated is KRAS mutant colorectal cancer (mCRC). In one embodiment, the cancer to be treated is non-squamous non-small cell lung cancer. In another embodiment, the cancer to be treated is head and neck squamous cell carcinoma.

In yet another aspect the invention relates to the in vitro use of an agent that specifically binds CD3 and CD16 for identifying a cancer patient as likely to respond to a therapy comprising an ADCC-enhanced antibody, wherein the level of CD3+ and CD16+ cell infiltration in the tumor of the patient prior to treatment is determined, wherein the level of CD3+ and CD16+ cell infiltration in the tumor above a reference level identifies that the patient is likely to respond to the therapy.

In one embodiment the agent comprises an antibody that specifically binds CD3 and an antibody that specifically binds CD16. In some embodiments, the level of CD3+ and CD16+ cell infiltration is determined in a tumor sample taken from the patient prior to treatment. In one embodiment, the level of CD3+ and CD16+ cell infiltration in the tumor prior to treatment is determined by immunohistochemical analysis. In another embodiment, the level of CD3+ and CD16+ cell infiltration in the tumor prior to treatment is determined by flow cytometric analysis.

In yet another embodiment, the level of CD3+ and CD16+ cell infiltration in the tumor prior to treatment is determined by Western Blot analysis. In still another embodiment, the level of CD3+ and CD16+ cell infiltration in the tumor prior to treatment is determined by ELISA. In one embodiment, the reference level is a value representative of the level of CD3+ and CD16+ cell infiltration in tumors prior to treatment of a population of patients who do not respond to a therapy comprising an ADCC-enhanced antibody. The reference level is representative of the level of CD3+ and CD16+ cell infiltration in tumors prior to treatment below which response would be expected. In one embodiment, the reference level is determined in vitro in tumor samples taken prior to treatment from patients who do not respond to a therapy comprising an ADCC-enhanced antibody. In one embodiment, response to the therapy with an ADCC-enhanced antibody is attributable to the ADCC activity of the antibody. In one embodiment, the level of CD3+ and CD16+ cell infiltration which is indicative for a patient who will respond to a therapy comprising an ADCC-enhanced antibody is at least 1.2-fold, at least 1.5-fold, at least 2-fold or at least 3-fold higher than the reference level.

In a further aspect the invention provides the use of an agent that specifically binds CD3 and CD16 for the manufacture of a diagnostics for assessing the likelihood of response of a cancer patient to a therapy comprising an ADCC-enhanced antibody, wherein the level of CD3+ and CD16+ cell infiltration in the tumor of the patient prior to treatment is determined, and wherein the level of CD3+ and CD16+ cell infiltration in the tumor prior to treatment above a reference level identifies that the patient is likely to respond to the therapy.

In one embodiment the agent comprises an antibody that specifically binds CD3 and an antibody that specifically binds CD16. In some embodiments, the level of CD3+ and CD16+ cell infiltration is determined in a tumor sample taken from the patient prior to treatment. In one embodiment, the level of CD3+ and CD16+ cell infiltration in the tumor prior to treatment is determined by immunohistochemical analysis. In another embodiment, the level of CD3+ and CD16+ cell infiltration in the tumor prior to treatment is determined by flow cytometric analysis. In yet another embodiment, the level of CD3+ and CD16+ cell infiltration in the tumor prior to treatment is determined by Western Blot analysis. In still another embodiment, the level of CD3+ and CD16+ cell infiltration in the tumor prior to treatment is determined by ELISA. In one embodiment, the reference level is a value representative of the level of CD3+ and CD16+ cell infiltration in tumors prior to treatment of a population of patients who do not respond to a therapy comprising an ADCC-enhanced antibody. The reference level is representative of the level of CD3+ and CD16+ cell infiltration in tumors prior to treatment below which response would be expected. In one embodiment, the reference level is determined in vitro in tumor samples taken prior to treatment from patients who do not respond to a therapy comprising an ADCC-enhanced antibody. In one embodiment, response to the therapy with an ADCC-enhanced antibody is attributable to the ADCC activity of the antibody. In one embodiment, the level of CD3+ and CD16+ cell infiltration which is indicative for a patient who will respond to a therapy comprising an ADCC-enhanced antibody is at least 1.2-fold, at least 1.5-fold, at least 2-fold or at least 3-fold higher than the reference level.

In one aspect, the present invention also provides a pharmaceutical composition comprising an ADCC-enhanced antibody for the treatment of a cancer patient in any of the above embodiments.

3. ADCC-Enhanced Antibodies

An ADCC-enhanced antibody as defined herein for the various aspects of the present invention is an antibody engineered to have increased ADCC activity as compared to a corresponding non-engineered antibody. In particular embodiments, the ADCC-enhanced antibody is a glycoengineered antibody comprising an increased proportion of non-fucosylated oligosaccharides in its Fc region, compared to a non-glycoengineered antibody. In one such embodiment, the antibody is produced in a host cell engineered to have increased β(1,4)-N-acetylglucosaminyltransferase III (GnTIII) activity, compared to a non-engineered host cell. In a more specific embodiment the host cell additionally is engineered to have increased α-mannosidase II (ManII) activity, compared to a non-engineered host cell. A host cell may be engineered to have increased β(1,4)-N-acetylglucosaminyltransferase III (GnTIII) activity by overexpression of one or more polypeptides having β(1,4)-N-acetylglucosaminyltransferase III (GnTIII) activity. Likewise, a host cell may be engineered to have increased α-mannosidase II (ManII) activity by overexpression of one or more polypeptides having α-mannosidase II (ManII) activity. This glycoengineering methodology has been described in greater detail in Umana et al., Nat Biotechnol 17, 176-180 (1999); Ferrara et al., Biotechn Bioeng 93, 851-861 (2006); WO 99/54342 (U.S. Pat. No. 6,602,684; EP 1071700); WO 2004/065540 (U.S. Pat. Appl. Publ. No. 2004/0241817; EP 1587921), WO 03/011878 (U.S. Pat. Appl. Publ. No. 2003/0175884), the entire content of each of which is incorporated herein by reference in its entirety.

In an alternative embodiment the ADCC-enhanced antibody is a glycoengineered antibody comprising an increased proportion of non-fucosylated oligosaccharides in its Fc region, compared to a non-glycoengineered antibody, wherein the antibody is produced in a host cell having decreased α(1,6)-fucosyltransferase activity. A host cell having decreased α(1,6)-fucosyltransferase activity may be a cell in which the α(1,6)-fucosyltransferase gene has been disrupted or otherwise deactivated, e.g. knocked out (see Yamane-Ohnuki et al., Biotech Bioeng 87, 614 (2004); Kanda et al., *Biotechnol Bioeng*, 94(4), 680-688 (2006); Niwa et al., J Immunol Methods 306, 151-160 (2006)).

In one embodiment, the ADCC-enhanced antibody is an antibody having at least about 50% non-fucosylated oligosaccharides in its Fc region. In one embodiment, the ADCC-enhanced antibody is an antibody having at least about 75% non-fucosylated oligosaccharides in its Fc region. In another embodiment, the ADCC-enhanced antibody is an antibody having at least about 50% bisected oligosaccharides in its Fc region. In one embodiment, the ADCC-enhanced antibody is an antibody having at least about 50% bisected, non-fucosylated oligosaccharides in its Fc region.

The oligosaccharide structures in the antibody Fc region can be analysed by methods well known in the art, e.g. by MALDI TOF mass spectrometry as described in Umana et al., Nat Biotechnol 17, 176-180 (1999) or Ferrara et al., Biotechn Bioeng 93, 851-861 (2006). The percentage of non-fucosylated oligosaccharides is the amount of oligosaccharides lacking fucose residues, relative to all oligosaccharides attached to Asn 297 (e.g. complex, hybrid and high mannose structures) and identified in an N-glycosidase F treated sample by MALDI TOF MS. Asn 297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. The percentage of bisected, or bisected non-fucosylated, oligosaccharides is determined analogously.

In one embodiment the ADCC-enhanced antibody is a full-length antibody of the IgG-class. In a particular embodiment, the ADCC-enhanced antibody is an IgG1 antibody. In one embodiment, the ADCC-enhanced antibody comprises a human Fc region, more particularly a human IgG Fc region, most particularly a human IgG1 Fc region. The ADCC-enhanced antibodies may comprise a human Ig gamma-1 heavy chain constant region, as set forth in SEQ ID NO: 1 (i.e. the antibodies are of human IgG1 subclass).

In certain embodiments the ADCC-enhanced antibody is directed to an antigen presented on a tumor cell. Particular target antigens of the ADCC-enhanced antibodies in the context of the present invention include antigens expressed on the surface of tumor cells, including, but not limited to, cell surface receptors such as epidermal growth factor receptor (EGFR), insulin-like growth factor receptors (IGFR) and platelet-derived growth factor receptors (PDGFR), prostate specific membrane antigen (PSMA), carcinoembryonic antigen (CEA), dipeptidyl peptidase IV (CD26, DPPIV), fibroblast activation protein (FAP), HER2/neu, HER-3, E-cadherin, CD20, melanoma-associated chondroitin sulfate proteoglycan (MCSP), c-Met, CUB domain-containing protein-1 (CDCP1), and squamous cell carcinoma antigen (SCCA).

In one embodiment, the ADCC-enhanced antibody is directed to an antigen selected from the group of CD20, EGFR, HER2, HER3, IGF-1R, CEA, c-Met, CDCP1, FAP and MCSP. In one embodiment, the ADCC-enhanced antibody is a multispecific antibody directed to two or more antigens selected from the group of CD20, EGFR, HER2, HER3, IGF-1R, CEA, c-Met, CDCP1, FAP and MCSP.

In a particular embodiment, the ADCC-enhanced antibody is an anti-EGFR antibody, more particularly an anti-human EGFR antibody. Suitable ADCC-enhanced anti-EGFR antibodies are described in WO 2006/082515 and WO 2008/017963, each of which is incorporated herein by reference in its entirety.

In a specific embodiment, the ADCC-enhanced antibody is a humanized, IgG1-subclass anti-EGFR antibody comprising a) in the heavy chain variable domain a CDR1 of SEQ ID NO: 2, a CDR2 of SEQ ID NO: 3, and a CDR3 of SEQ ID NO: 4, and b) in the light chain variable domain a CDR1 of SEQ ID NO: 5, a CDR2 of SEQ ID NO: 6, and a CDR3 of SEQ ID NO: 7.

In an even more specific embodiment, the ADCC-enhanced antibody is a humanized, IgG1-subclass anti-EGFR antibody comprising the heavy chain variable domain of SEQ ID NO: 8 and the light chain variable domain of SEQ ID NO: 9.

In another specific embodiment, the ADCC-enhanced antibody is a humanized, IgG1-subclass anti-EGFR antibody comprising a) in the heavy chain variable domain a CDR1 of SEQ ID NO: 2, a CDR2 of SEQ ID NO: 3, and a CDR3 of SEQ ID NO: 4, and b) in the light chain variable domain a CDR1 of SEQ ID NO: 5, a CDR2 of SEQ ID NO: 6, and a CDR3 of SEQ ID NO: 7, wherein the antibody is glycoengineered to have an increased proportion of non-fucosylated oligosaccharides in its Fc region compared to a corresponding non-glycoengineered antibody.

In a more specific embodiment, the ADCC-enhanced antibody is a humanized, IgG1-subclass anti-EGFR antibody comprising the heavy chain variable domain of SEQ ID NO: 8 and the light chain variable domain of SEQ ID NO: 9, wherein the antibody is glycoengineered to have an increased proportion of non-fucosylated oligosaccharides in its Fc region compared to a corresponding non-glycoengineered antibody.

In yet another specific embodiment, the ADCC-enhanced antibody is a humanized, IgG1-subclass anti-EGFR antibody comprising a) in the heavy chain variable domain a CDR1 of SEQ ID NO: 2, a CDR2 of SEQ ID NO: 3, and a CDR3 of SEQ ID NO: 4, and b) in the light chain variable domain a CDR1 of SEQ ID NO: 5, a CDR2 of SEQ ID NO: 6, and a CDR3 of SEQ ID NO: 7, and c) in the Fc region at least 50% non-fucosylated oligosaccharides.

In a more specific embodiment, the ADCC-enhanced antibody is a humanized, IgG1-subclass anti-EGFR antibody comprising the heavy chain variable domain of SEQ ID NO: 8, the light chain variable domain of SEQ ID NO: 9, the heavy chain constant region of SEQ ID NO: 1, and at least 50% non-fucosylated oligosaccharides in the Fc region.

In one embodiment the ADCC-enhanced antibody is imgatuzumab.

4. Cancer Types

The present invention is useful in different types of cancer. In particular embodiments according to the invention, the cancer is a solid tumor. In one such embodiment, the cancer is selected from the group consisting of colorectal cancer, lung cancer, head and neck cancer, breast cancer, pancreatic cancer, renal cancer, ovarian cancer, gastric cancer and skin cancer. In one embodiment, the cancer is non-small cell lung carcinoma (NSCLC). In a more specific embodiment, the cancer is squamous and non-squamous NSCLC. In another embodiment, the cancer is colorectal carcinoma (CRC). In a more specific embodiment, the cancer is KRAS mutant colorectal cancer (mCRC). In yet another embodiment, the cancer is head and neck squamous cell carcinoma (HNSCC). In one embodiment the cancer is selected from the group consisting of NSCLC, CRC and HNSCC.

5. Combinations of Markers

The biomarker of the present invention, i.e. the level of CD3+ and CD16+ cell infiltration prior to treatment, can be combined with other biomarkers to biomarker sets. Biomarker sets can be built from any combination of predictive biomarkers to make predictions about the effect of ADCC-enhanced antibody treatment in cancer patients. For example, the level of CD3+ and CD16+ cell infiltration prior to treatment might be combined with the expression level of the target antigen of the ADCC-enhanced antibody to a biomarker set.

6. Determination of Infiltration Levels of CD3+ Cells and CD16+ Cells

In particular embodiments, the level of CD3+ and CD16+ cell infiltration is determined by contacting a tumor sample from the patient with an agent that specifically binds to CD3+ cells and CD16+ cells, thereby forming a complex between the agent and the CD3+ cells and CD16+ cells, detecting the amount of complex formed, and thereby measuring the level of CD3+ and CD16+ cell infiltration. In some embodiments said agent comprises an antibody that specifically binds to CD3 and an antibody that specifically binds to CD16. In some embodiments, the amount of complex formed is detected by immunohistochemical analysis. In other embodiments, the amount of complex formed is detected by flow cytometric analysis.

In other embodiments, the level of CD3+ and CD16+ cell infiltration is determined by contacting a tumor sample from the patient with an agent the specifically binds to CD3 and CD16 protein, thereby forming a complex between the agent and the CD3 and CD16 protein, detecting the amount of complex formed, and thereby measuring the level of CD3+ and CD16+ cell infiltration. In some embodiments said agent comprises an antibody that specifically binds to CD3 and an antibody that specifically binds to CD16. In some embodiments, the amount of complex formed is detected by Western Blot analysis. In other embodiments, the amount of complex formed is detected by enzyme-linked immunosorbent assay (ELISA).

In other embodiments, the level of CD3+ and CD16+ cell infiltration is determined by contacting a tumor sample from the patient with an agent the specifically binds to CD3 and CD16 mRNA or cDNA, thereby forming a complex between the agent and the CD3 and CD16 mRNA or cDNA, detecting the amount of complex formed, and thereby measuring the level of CD3+ and CD16+ cell infiltration. In some embodiments said agent comprises a nucleic acid probe that specifically binds to CD3 mRNA or cDNA and a nucleic acid probe that specifically binds to CD16 mRNA or cDNA. In some embodiments, the amount of complex formed is detected by quantitative PCR analysis. In other embodiments, the amount of complex formed is detected by microarray analysis.

The level of CD3+ and CD16+ cell infiltration may be assessed by any method known in the art suitable for visualizing cells in patient tissues, such as immunohistochemical or immunofluorescent methods using anti-CD3 and anti-CD16 antibodies. In a particular embodiment, the level of CD3+ and CD16+ cell infiltration is determined by immunohistochemical analysis. A suitable anti-CD16 antibody that can be used for detection of CD16+ cells by immunohistochemistry is, for example, the anti-CD16 antibody clone 2H7 (Biogenex). A suitable anti-CD3 antibody that can be used for detection of CD3+ cells by immunohistochemistry is, for example, the anti-CD3 antibody clone 2GV6 (Ventana Medical Systems, Inc.).

In an alternative embodiment, the level of CD3+ and CD16+ cell infiltration is determined by flow cytometric analysis. Flow cytometric methods (FACS) are well known in the art for the quantification of cells in tissue samples. In particular, they allow determining the number of cells expressing a specific antigen (e.g. CD3+ and CD16+ cells) among a defined total number of cells in a tissue sample (e.g. a (part of) a tumor biopsy).

The level of CD3+ and CD16+ cell infiltration may also be determined indirectly, by quantification of CD3+ and CD16 protein or mRNA levels in patient tissues. Suitable methods known in the art for the determination of specific protein levels include immunoassay methods such as enzyme-linked immunosorbent assay (ELISA), methods for determination of mRNA levels include for example quantitative RT-PCR or microarray technologies.

All the above mentioned methods and technologies are well known in the art and can be deduced from standard textbooks such as Lottspeich (Bioanalytik, Spektrum Akademisher Verlag, 1998) or Sambrook and Russell (Molecular Cloning: A Laboratory Manual, CSH Press, Cold Spring Harbor, N.Y., U.S.A., 2001).

In particular embodiments, the level of CD3+ and CD16+ cell infiltration is determined in a biopsy taken from the tumor of the cancer patient, in particular taken from the primary tumor of the cancer patient, prior to treatment.

7. Methods of Treatment

In the context of the present invention, an ADCC-enhanced antibody such as imgatuzumab is to be administered alone or in addition (in all potential sequences and schedules) to or as a co-therapy or co-treatment with one or more chemotherapeutic agents administered as part of standard chemo/radio therapy regimen as known in the art. Examples of agents included in such standard chemotherapy regimens include 5-fluorouracil, leucovorin, irinotecan, gemcitabine, erlotinib, capecitabine, taxanes, such as docetaxel and paclitaxel, interferon alpha, vinorelbine, and platinum-based chemotherapeutic agents, such as, carboplatin, cisplatin and oxaliplatin.

Common modes of administration include parenteral administration as a bolus dose or as an infusion over a set period of time, e.g., administration of the total daily dose over 10 min., 20 min., 30 min., 40 min., 50 min., 60 min., 75 min., 90 min., 105 min., 120 min., 3 hr., 4 hr., 5 hr. or 6 hr. For example, 2.5 mg/kg of body weight to 25 mg/kg of body weight ADCC-enhanced antibody such as imgatuzumab can be administered every week, every 2 weeks or every 3 weeks, depending on the type of cancer being treated. Examples of dosages include 2.5 mg/kg of body weight, 5 mg/kg of body weight, 7.5 mg/kg of body weight, 10 mg/kg of body weight, 15 mg/kg of body weight, 20 mg/kg of body weight and 25 mg/kg of body weight given every week, every 2 weeks or every 3 weeks. Further examples of dosages are 700 mg weekly or every 2 weeks, 1000 mg weekly or every 2 weeks, 1400 mg weekly or every two weeks, 700 mg every 3 weeks, 1000 mg every 3 weeks, and 1400 mg every 3 weeks.

The skilled person will recognize that further modes of administration and dosages of ADCC-enhanced antibody such as imgatuzumab are encompassed by the invention as determined by the specific patient and chemotherapy regimen, and that the specific mode of administration and therapeutic dosage are best determined by the treating physician according to methods known in the art.

8. Kit

The present invention also relates to a diagnostic composition or kit comprising one or more compounds for detecting the level of CD3+ and CD16+ cell infiltration. As detailed herein, anti-CD3 and anti-CD16 antibodies may be of use for detecting CD3 and CD16 protein and may thus be comprised in a kit according to the invention. Such antibodies may be labelled (e.g. with a fluorescent label, a radiolabel, an enzymatic label or a biotin/avidin complex) to enable their direct detection, or may be used in combination with labelled secondary antibodies (i.e. antibodies that specifically bind to specific other antibodies such as antibodies from a particular host species). Appropriate secondary antibodies may thus also be comprised in the kit. Further components may be reagents needed for carrying out the detection, e.g. buffers, fixatives, blocking reagents, diluents, chromogens, enzymes etc. for immunohistochemistry, immunofluorescence, ELISA, Western Blotting or whatever the detection method of choice may be. Alternatively, if CD3 and CD16 mRNA is to be detected, the kit may comprise oligonucleotides such as primers and fluorescent probes for real-time PCR, enzymes for preparation of cDNA such as reverse transcriptase, and the like.

In a further aspect of the invention, the kit of the invention may advantageously be used for carrying out a method of the invention and could be, inter alia, employed in a variety of applications, e.g., in the diagnostic field or as a research tool. The parts of the kit of the invention can be packaged individually in vials or in combination in containers or multicontainer units. Manufacture of the kit follows preferably standard procedures which are known to the person skilled in the art. The kit or diagnostic compositions may be used for detection of the level of CD3+ and CD16+ cell infiltration in tumors in accordance with the herein-described methods of the invention, employing, for example, immunohistochemical techniques described herein.

EXAMPLES

The present invention is further illustrated by the following non-limiting illustrative examples.

Example 1

Extension Part of Phase I Study BO21495 in KRAS Mutant CRC

Study Design

BO21495 is an open-label, multicentre, non-randomised, dose-escalating, phase I study of imgatuzumab in patients with solid tumors which consisted of two parts: a dose escalation part (Paz Ares et al. (2011), J Clin Oncol 29, 3783-90) and an extension part. The second part of the study enrolled 25 patients with KRAS-mutant colorectal carcinoma (CRC) were treated, who received a flat dose of 1400 mg imgatuzumab administered intravenously (i.v.) on day 1 and 8 followed by dosing every 2 weeks (q2W), based on the safety profile and efficacy demonstrated in the first part of the study.

Patient Selection

Eligible patients were aged ≥18 years with an Eastern Cooperative Oncology Group performance status of ≤1 and adequate haematology, blood chemistry, renal and liver function. Patients had histologically/cytologically confirmed metastatic EGFR-positive and KRAS-mutant CRC with radiologically measurable progressive disease (PD). Patients with more than two previous cytotoxic regimens for metastatic disease were excluded. All patients gave written informed consent and approval from local Ethics Committees was obtained. The study was conducted in accordance with Good Clinical Practice guidelines.

Demographics

Median age was 63 years (range 50-80). All patients had metastatic disease at baseline (frequently involving the liver [18/25 patients] and lung [17/25 patients]). All patients received a maximum of two chemotherapy regimens for their metastatic disease and two had previously received cetuximab-containing regimens.

TABLE 1

Patient characteristics and baseline demographics

| | Entire cohort (n = 25) |
|---|---|
| Sex, n (%) | |
| Male | 14 (56%) |
| Female | 11 (44%) |
| Age, median (range) | 63 (50-80) |
| ECOG performance status at screening, n (%) | |
| 0 | 10 (40%) |
| 1 | 15 (60%) |
| Disease extent at first diagnosis | |
| Metastatic | 12 (48%) |
| Prior therapeutic regimens,[a] n (%) | |
| Oxaliplatin-containing | 25 (100%) |
| Irinotecan-containing | 23 (92%) |
| Bevacizumab-containing | 14 (56%) |
| Cetuximab-containing | 2 (8%) |
| EGFR membrane staining, H-score, median (range)[b] | 3% (1-81%) |
| KRAS mutational status | |
| GLY12ALA | 3 (12%) |
| GLY12ASP | 7 (28%) |
| GLY12CYS | 3 (12%) |
| GLY12VAL | 6 (24%) |
| GLY13ASP | 5 (20%) |
| GLN61LEU | 1 (4%) |

26 patients were enrolled to the trial; however one patient withdrew consent before starting treatment.
[a]As specified in the inclusion criteria, patients had no more than two previous cytotoxic regimens for metastatic disease;
[b]Evaluated at baseline in archival specimens.
ECOG, Eastern Cooperative Oncology Group; EGFR, epidermal growth factor receptor.

Administration of the Drug

The first dose of imgatuzumab was administered at an initial infusion rate of 10 mg/hour. After one hour, infusion rates were escalated every 30 minutes up to 800 mg/hour. Subsequent infusions began at 20 mg/hour if the first infusion was well tolerated. Premedication with paracetamol, antihistamine and corticosteroids was given for the first two infusions, to minimise the risk of infusion-related reactions (IRRs).

Tumor Biopsies

Optional tumour biopsies for immunohistochemistry were taken pre-treatment at baseline. For eleven patients a tumor biopsy prior (generally not more than two weeks) to the first imgatuzumab infusion was available (others did not agree to the biopsy or biopsy was medically contra-indicated). However, for technical reasons not all parameters could be assessed on all eleven tumor samples. Biopsies were formalin-fixed and paraffin-embedded, and analysed for immune effector cell infiltrates by immunohistochemistry (IHC). Tumour-infiltrating immune effector cells were graded by counting the number of positive staining cells/mm$^2$.

Immunohistochemical Analysis

IHC was performed on a Ventana Benchmark XT system. Deparaffinized slides were incubated for 1 hour with the anti-CD16 antibody clone 2H7 (Biogenex) diluted 1:10 in antibody diluent (Ventana #251-018). CD3 expression was detected by using the anti-CD3 antibody clone 2GV6 (Ventana). The Ultra View™ Universal DAB detection kit (Ventana) was used for detection, followed by 4 minutes incubation with hematoxylin II (Ventana #790-2208) and 4 minutes bluing post counterstain (Ventana #760-2037). An isotype-matched mouse IgG (Ventana #760-2014) was used for negative controls.

Quantification of Immune Cell Infiltrates in Tumors

CD3+ and CD16+ cells were counted in fields of view under a light microscope having a grid (5×5 fields) in the eyepiece. Cells were counted in up to 25 randomly selected fields at a magnification of 400× and the density of cells, i.e. the number of cells per $mm^2$ of tissue area was calculated. Cells were counted in the central tumor as well as in the tissue in close proximity to the tumor cells.

Assessment of Tumor Response

Tumour assessment was performed by CT or MRI scan at screening and every 8 weeks beginning at cycle 4 according to modified RECIST (Response Evaluation Criteria In Solid Tumours) criteria v1.0.

Statistical Considerations

Correlation of the percent change of the sum of longest diameter (SLD) from baseline to the best post-baseline tumor assessment and staining of CD3+ and CD16+ cells in tumor biopsies obtained at baseline was evaluated with Spearman's rank correlation coefficient.

Results

Figure 2:
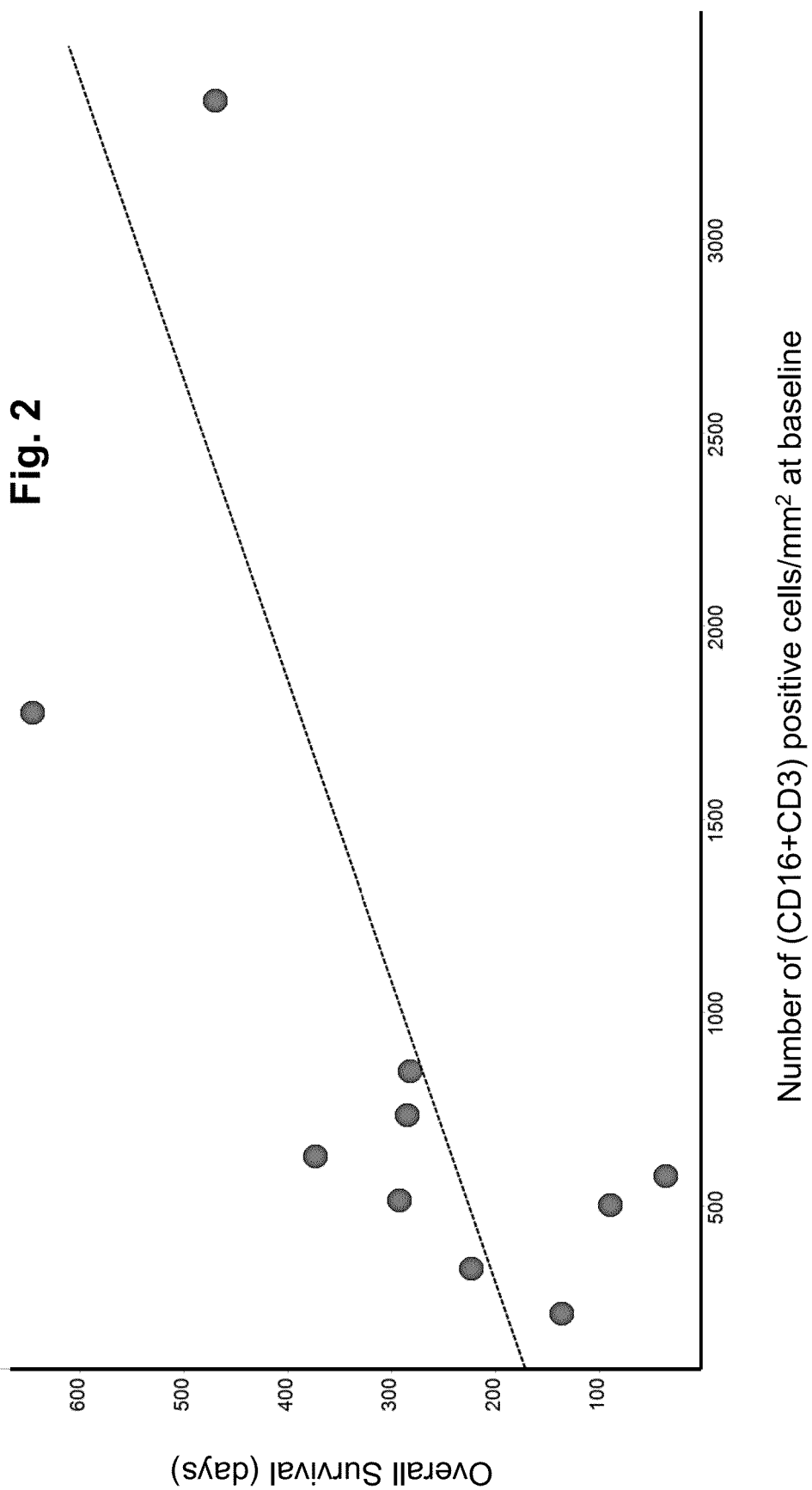
FIG. 2 (from extension cohort of phI BO21495 in KRAS mutant colorectal cancer (mCRC) patients) shows the correlation between the overall survival (OS) from baseline and baseline staining in new tumour biopsies obtained at baseline for the sum of CD3+ and CD16+ cells. The dotted line represents the straight line fit.

Correlative analysis of baseline biomarkers with best tumor response showed that an increased number of tumor infiltrating cells staining positive for CD3 and CD16 was proportional to a lesser increase in tumor size (r=−0.74, n=10; see FIG. 1). Additionally, the correlation between the overall survival (OS) and baseline staining for CD3 and CD16 showed a higher OS in patients with higher baseline infiltration of CD3+ and CD16+ cells (r=0.67, n=10, see FIG. 2).

Example 2

Non-Squamous Histology of BP22349 in Non-Small Cell Lung Cancer (NSCLC)

Study Design

This was a multicenter, open-label phase Ib study of imgatuzumab in combination with cisplatin and gemcitabine/pemetrexed in patients with advanced or recurrent EGFR-positive non-small cell lung cancer (NSCLC).

Patients were grouped into two groups according to the histology of their tumors (squamous or non-squamous), which were evaluated separately. So far, the phase Ib part of the study has been completed for the non-squamous histology group which is reported here.

Patients in this group (a total of 14 patients) were treated with 2 different doses of imgatuzumab in combination with cisplatin and pemetrexed according to the following dosage regimen:

Cohort 1:
For a maximum of 6 chemotherapy cycles (18 weeks):
Cisplatin 75 $mg/m^2$ i.v. on day 1 q3W (three-weekly) and pemetrexed 500 $mg/m^2$ i.v. on day 1 q3W for a maximum of 6 cycles.
imgatuzumab 1000 mg i.v. (day 1, 8) followed by 1000 mg q2W (two-weekly) i.v.
Followed by:
imgatuzumab 1400 mg q2W i.v. until disease progression, unacceptable toxicity or withdrawal of consent.

Cohort 2:
For a maximum of 6 chemotherapy cycles (18 weeks):
Cisplatin 75 $mg/m^2$ i.v. on day 1 q3W and pemetrexed 500 $mg/m^2$ i.v. on day 1 q3W for a maximum of 6 cycles.
imgatuzumab 1400 mg i.v. (day 1, 8) followed by 1400 mg q2W i.v.
Followed by:
imgatuzumab 1400 mg q2W i.v. until disease progression, unacceptable toxicity or withdrawal of consent Patient Selection Eligible patients were aged ≥18 years with an Eastern Cooperative Oncology Group performance status of ≤1 and adequate haematology, blood chemistry, renal and liver function. Patients had histologically documented inoperable, locally advanced (stage IIIb), metastatic (stage IV) or recurrent NSCLC. Patients with prior chemotherapy or treatment with another systemic anti-cancer agent were excluded. All patients gave written informed consent and approval from local Ethics Committees was obtained. The study was conducted in accordance with Good Clinical Practice guidelines.

Administration of the Drug

Infusion rate for imgatuzumab was 10 mg/h for the first hour. Thereafter, if tolerated by the patient, the infusion rate was escalated in 30 minute intervals up to a maximum of 400 mg/h. If the first infusion was well tolerated (i.e. no serious infusion-related reactions were observed), the second infusion started at 20 mg/h for 30 minutes, followed by escalation of the infusion rate in 30 minute intervals up to 800 mg/h. Subsequent infusions started at an infusion rate of 50 mg/h, followed by escalation in 15 minute intervals up to 800 mg/h, provided the previous infusion was well tolerated by the patient. Otherwise the same infusion schedule as for the first infusion was applied.

Cisplatin and pemetrexed were administered according to local prescribing information. In general, pemetrexed should be administered at 500 $mg/m^2$ i.v. over 10 minutes, followed by a 30 minutes break before cisplatin administration, and cisplatin should be administered at 75 $mg/m^2$ i.v. over 2 hours.

Vitamin $B_{12}$ and folic acid according to the local prescribing information were given as pre-medication pemetrexed administration (day −7 to day −1). Paracetamol, antihistamine and corticosteroids were given as premedication for the first (day −1 to day 2) and second imgatuzumab infusion (on the day of the second infusion).

Tumor Biopsies

Archival tumor specimens from diagnosis or fresh tumor biopsies taken within 21 days prior to the first administration of any study drug were collected. Biopsies were formalin-fixed and paraffin-embedded, and analysed for immune effector cell infiltrates by immunohistochemistry (IHC). Tumour-infiltrating immune effector cells were graded by counting the number of positive staining cells/$mm^2$. Immunohistochemical analysis and quantification of immune cell infiltrates was performed as described above (see Example 1).

Assessment of Tumor Response

Baseline tumor assessment was done within 21 days prior to the first administration of any study drug by chest-abdominal CT scan (or MRI). Post-baseline assessments were performed every six weeks after baseline, i.e. on cycle 3 day 1, cycle 5 day 1 etc. until progression or withdrawal of consent.

Tumor response was evaluated according to RECIST (Response Evaluation Criteria in Solid Tumors) version 1.1 (Eisenhauer et al. (2009), Eur J Cancer 45, 228-247).

Statistical Considerations

Correlation of the percent change of the sum of longest diameter (SLD) from baseline to the best post-baseline tumor assessment and staining of CD3+ and CD16+ cells in tumor biopsies obtained at baseline was evaluated with Spearman's rank correlation coefficient.

Results

Figure 3:
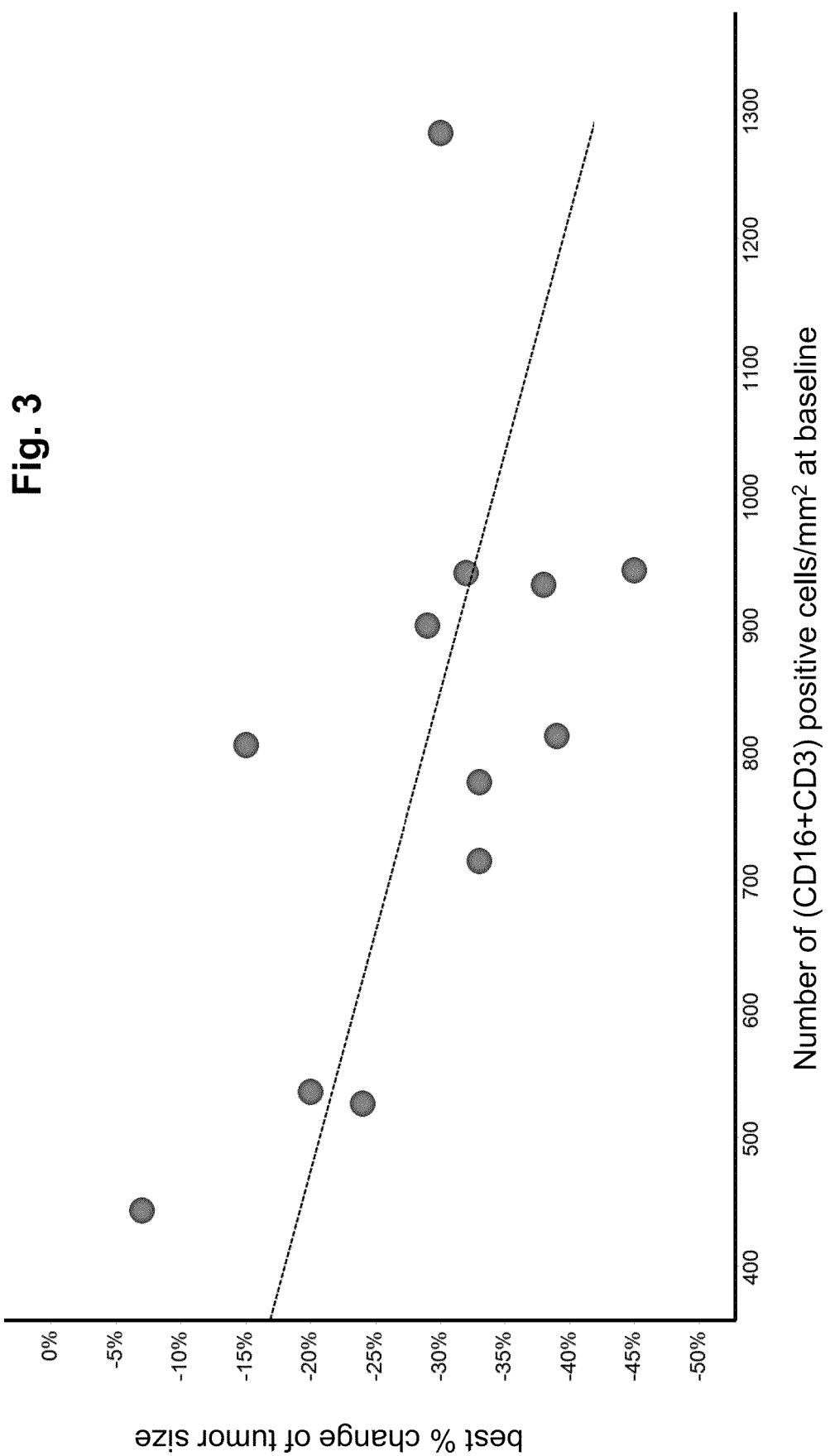
FIG. 3 (from phIb BP22349 study in non-squamous non-small cell lung cancer patients) shows the correlation between the best percent change of the sum of longest diameter (SLD) from baseline (independent review assessment) and baseline staining in tumour biopsies obtained at baseline for the sum of CD3+ and CD16+ cells. The dotted line represents the straight line fit.
Figure 4:
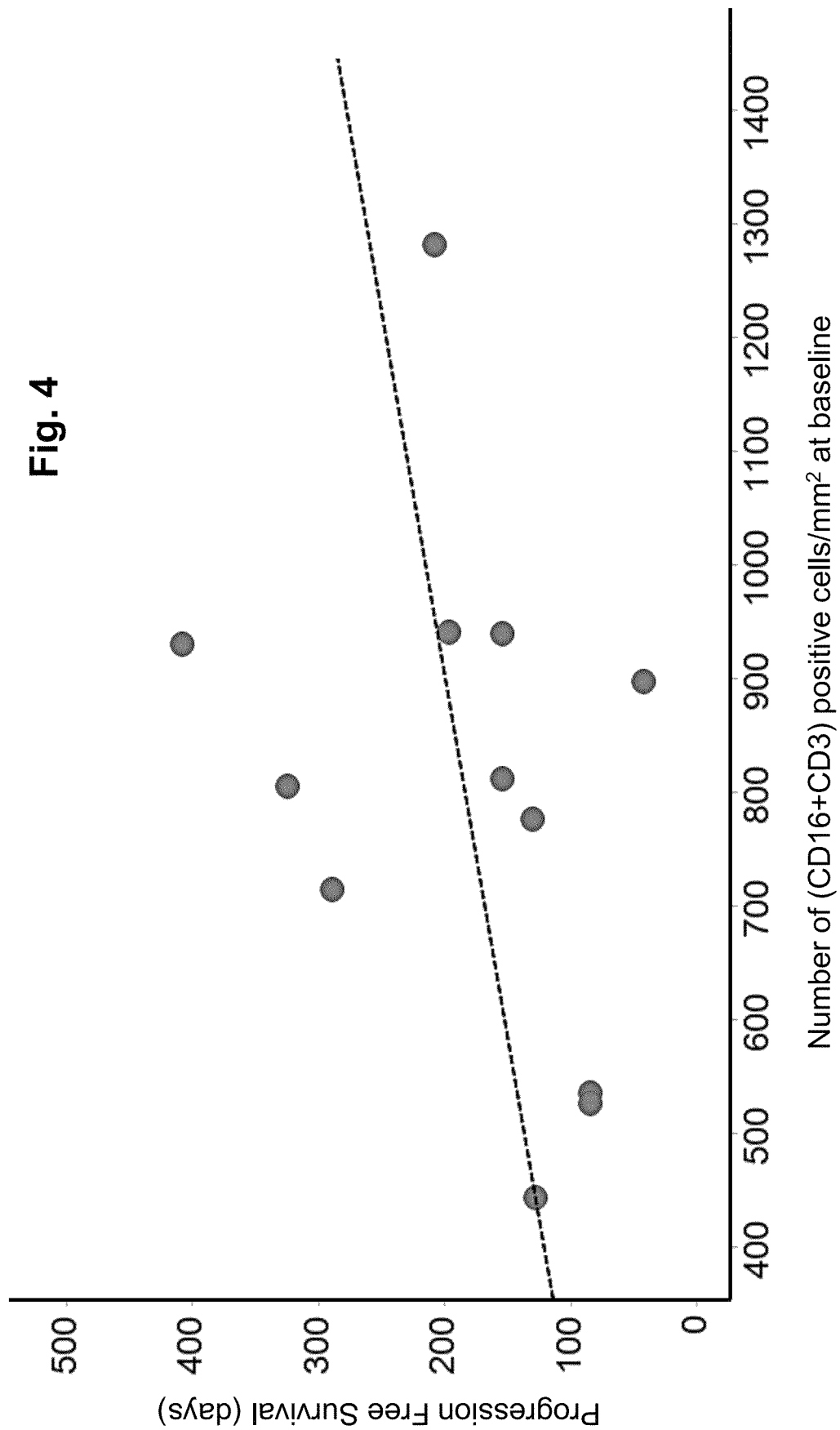
FIG. 4 (from phIb BP22349 study in non-squamous non-small cell lung cancer patients) shows the correlation between the progression free survival (PFS) from baseline (independent review assessment) and baseline staining in tumour biopsies obtained at baseline for the sum of CD3+ and CD16+ cells. The dotted line represents the straight line fit.
Figure 5:
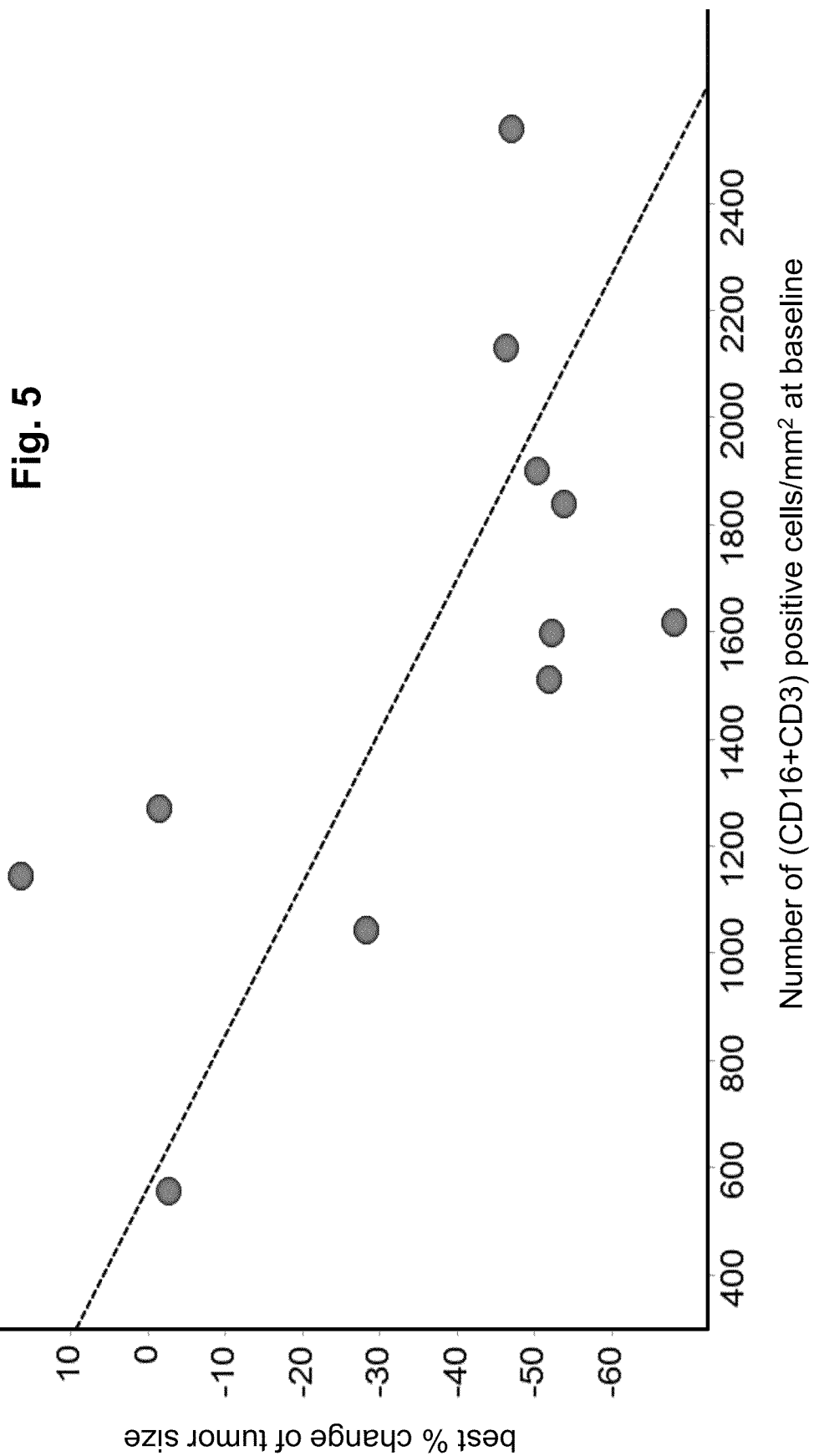
FIG. 5 (from phI BP22350 Mode of Action study in head and neck squamous cell carcinoma patients) shows the correlation between the SUV$_{max}$ reduction from baseline to the post-baseline tumour assessment at around 3 weeks and baseline staining in new tumour biopsies obtained at baseline for the sum of CD3+ and CD16+ cells. The dotted line represents the straight line fit.
Figure 6:
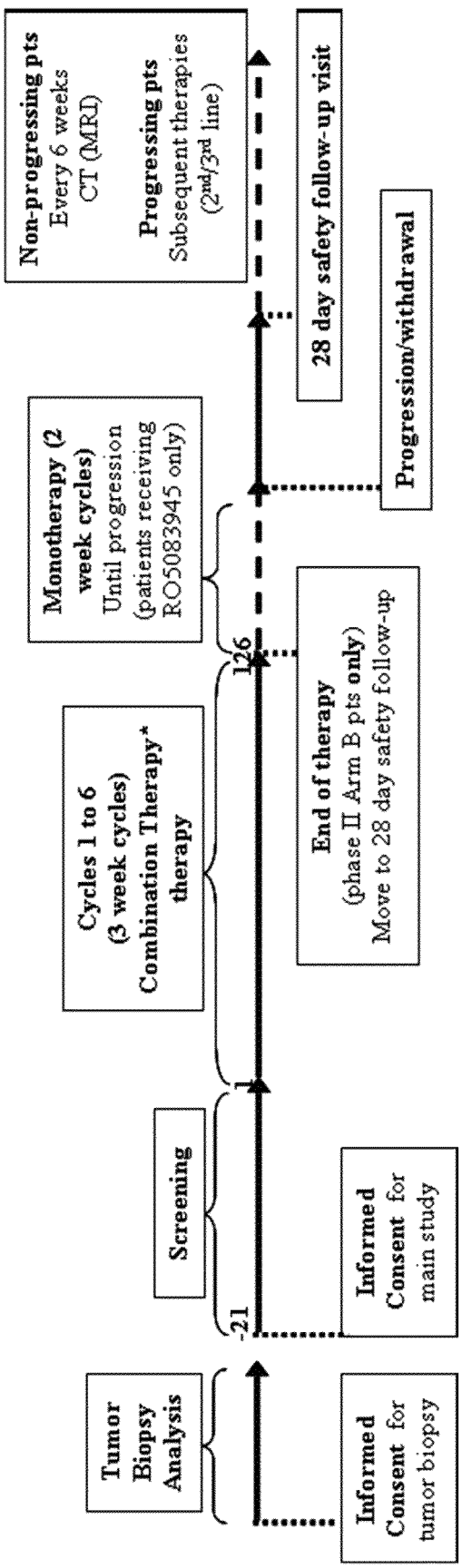
FIG. 6 shows a schematic of the study design for phIb BP22349 study in non-small cell lung cancer patients.

Correlative analysis of baseline biomarkers with best tumor response showed that an increased number of tumor infiltrating cells staining positive for CD3 and CD16 was proportional to a greater decrease in tumor size (r=−0.57, n=12; see FIG. 3). Additionally, the correlation between the progression free survival (PFS) and baseline staining for CD3 and CD16 showed a higher PFS in patients with higher baseline infiltration of CD3+ and CD16+ cells (r=0.33, n=10, see FIG. 4).

Example 3

Phase I Mode of Action Study BP22350 in Head and Neck Squamous Cell Carcinoma (HNSCC)

Study Design

This was an exploratory, open-label multicenter study to investigate the pharmacodynamics of imgatuzumab, compared to cetuximab, in previously untreated patients with operable head and neck squamous cell carcinoma (HNSCC).

Treatments for this study were performed during the patient's waiting period before surgery (neoadjuvant setting). Patients were treated either with 700 mg imgatuzumab on day 1 and 8 (maximum of 4 infusions due to logistical reasons), or with 400 mg cetuximab per m$^2$ body surface area on day 1 and 250 mg/m$^2$ cetuximab on day 8, followed by surgical removal of tumors 7 days after the last infusion.

Patient Selection

Eligible patients were aged ≥18 years with an Eastern Cooperative Oncology Group performance status of ≤2 and adequate haematology, blood chemistry, renal and liver function. Patients had histologically confirmed squamous cell carcinoma of the oral cavity, oropharynx, hypopharynx or larynx. Tumors had to be considered resectable with a planned surgical excision, and patients had to be naïve for chemo- and radiotherapy. All patients gave written informed consent and approval from local Ethics Committees was obtained. The study was conducted in accordance with Good Clinical Practice guidelines.

Administration of the Drug

Infusion rate for imgatuzumab was 10 mg/h for the first hour. Thereafter, if tolerated by the patient, the infusion rate was escalated in 30 minute intervals up to a maximum of 300 mg/h. If the first infusion was well tolerated (i.e. no serious infusion-related reactions were observed), subsequent infusions started at 20 mg/h for 30 minutes, followed by escalation of the infusion rate in 30 minute intervals up to 300 mg/h. Otherwise the same infusion schedule as for the first infusion was applied.

Cetuximab was administered according to local prescribing information. The recommended infusion period was 120 minutes for the first dose, and 60 minutes for the second dose. The maximum infusion rate was 10 mg/min.

For imgatuzumab infusions, pre-medication with paracetamol, anti-histamine and corticosteroid was done, for cetuximab infusions pre-medication with anti-histamine and corticosteroid was done according to local prescribing information.

Tumor Biopsies

Tumor biopsies (3-5 mm) were taken within 21 days prior to the first dosing, after the first FDG-PET/CT scan. Biopsies were formalin-fixed and paraffin-embedded, and analysed for immune effector cell infiltrates by immunohistochemistry (IHC). Tumour-infiltrating immune effector cells were graded by counting the number of positive staining cells/mm$^2$. Immunohistochemical analysis and quantification of immune cell infiltrates was performed as described above (see Example 1).

Assessment of Tumor Response

Tumors were assessed by radiologic imaging (2-$^{18}$F-fluoro-2-deoxy-D-glucose(FDG)-PET/CT scans) prior to any intervention (including the tumor biopsy) on days −21 to −1, as well as before surgery (not more than 3 days before surgery).

FDG-PET Scans

Patients had to fast for at least 4-6 hours prior to the FDG-PET scan. Blood glucose level was checked (typically at the PET center) on the day of the FDG-PET scan and results assessed prior to the administration of FDG. The patient should have a blood glucose level≤180 mg/dL (≤10 mmol/mL) in order to have the FDG-PET scan. The interval between FDG administration and scanning was 60 minutes±10 minutes and care was taken to keep the time interval between injection and start of the scan the same at follow-up compared to baseline.

Scan Acquisition

Attenuation corrected FDG-PET scans (from skull base to mid-thigh) were performed. The patient was administered 370-740 MBq (10-20 mCi) FDG intravenously (injected activity was dependent on local practice and scanner type) (Shankar et al. (2006), J Nucl Med 47, 1059-66). The administered activity and time of FDG administration and body weight on the day of scanning was recorded for subsequent calculation of maximum tumor standardized uptake value (SUV$_{max}$). Approximately one hour following the administration of FDG, a whole body PET scan (base of skull to thighs) and/or a separate head and neck view was performed. Initial and follow-up scans were done the same way, taking particular care to keep the interval between FDG administration and scanning as consistent as possible.

Wherever possible, a PET/CT scanner was used (as opposed to a dedicated PET scanner) to allow for correction of the emission scan by a low dose CT transmission scan.

Scan Interpretation

The PET/CT scans were analyzed visually and interpreted and compared qualitatively by an experienced reader. A patient had to have at least two PET scans for exploratory FDG-PET response assessment. The tumor uptake was analyzed semi-quantitatively by SUVmax according to the following equation:

SUV$_{max}$=[maximum radiotracer concentration in tumor (kBq/mL;μCi/mL)×body weight (kg)]/injected dose (MBq;mCi)

The change in SUV$_{max}$ was assessed. European Organization for Research and Treatment of Cancer (EORTC) response criteria were employed for evaluation of tumor response (Young et al. (1999), Eur J Cancer 35, 1773-82).

Statistical Considerations

Correlation of the percent change of the SUV from baseline to the post-baseline tumor assessment at 2 weeks and staining of CD3+ and CD16+ cells in tumor biopsies obtained at baseline was evaluated with Spearman's rank correlation coefficient.

Results

Correlative analysis of baseline biomarkers with tumor response at 2 weeks showed that an increased number of tumor infiltrating cells staining positive for CD3 and CD16 was proportional to a greater reduction in SUV$_{max}$ in the patient group treated with imgatuzumab (r=−0.65, n=11; see FIG. 3).

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

REFERENCES

Galon J, Costes A, Sanchez-Cabo F, et al. Type, density, and location of immune cells within human colorectal tumors predict clinical outcome. Science 2006; 313: 1960-4.

Fridman W H, Galon J, Dieu-Nosjean M C, et al. Immune infiltration in human cancer: prognostic significance and disease control. Curr Top Microbiol Immunol. 2011; 344: 1-24.

Halama N, Braun M, Kahlert C, et al. Natural killer cells are scarce in colorectal carcinoma tissue despite high levels of chemokines and cytokines. Clin Cancer Res. 2011; 17(4): 678-89.

Hiraoka K, Miyamoto M, Cho Y, et al. Concurrent infiltration by CD8+ T cells and CD4+ T cells is a favourable prognostic factor in non-small-cell lung carcinoma. Br J Cancer. 2006; 94(2):275-80.

Al-Shibli K I, Donnem T, Al-Saad S, Persson M, Bremnes R M, Busund L T. Prognostic effect of epithelial and stromal lymphocyte infiltration in non-small cell lung cancer. Clin Cancer Res. 2008; 14(16):5220-7.

Kawai O, Ishii G, Kubota K, et al. Predominant infiltration of macrophages and CD8(+) T Cells in cancer nests is a significant predictor of survival in stage IV nonsmall cell lung cancer. Cancer. 2008; 113(6):1387-95.

Welsh T J, Green R H, Richardson D, Waller D A, O'Byrne K J, Bradding P. Macrophage and mast-cell invasion of tumor cell islets confers a marked survival advantage in nonsmall-cell lung cancer. J Clin Oncol. 2005; 23: 8959-67.

Dieu-Nosjean M C, Antoine M, Danel C, et al. Long-term survival for patients with non-small-cell lung cancer with intratumoral lymphoid structures. J Clin Oncol. 2008; 26:4410-17.

Brandwein-Gensler M, Teixeira M S, Lewis C M, et al. Oral squamous cell carcinoma: histologic risk assessment, but not margin status, is strongly predictive of local disease-free and overall survival. Am J Surg Pathol. 2005; 29(2): 167-78.

Zhang Y L, Li J, Mo H Y, et al. Different subsets of tumor infiltrating lymphocytes correlate with NPC progression in different ways. Mol Cancer. 2010; 9:4.

Badoual C, Hans S, Rodriguez J, et al. Prognostic value of tumor-infiltrating CD4+ T-cell subpopulations in head and neck cancers. Clin Cancer Res. 2006; 12(2):465-72.

Rajjoub S, Basha S R, Einhorn E, Cohen M C, Marvel D M, Sewell D A. Prognostic significance of tumor-infiltrating lymphocytes in oropharyngeal cancer. Ear Nose Throat J. 2007; 86:506-11.

Le Q T, Shi G, Cao H, et al. Galectin-1: a link between tumor hypoxia and tumor immune privilege. J Clin Oncol. 2005; 23:8932-41.

Zhang L, Conejo-Garcia J R, Katsaros D, et al. Intratumoral T cells, recurrence, and survival in epithelial ovarian cancer. N Engl J Med. 2003; 348(3):203-13.

Marcus B, Arenberg D, Lee J, et al. Prognostic factors in oral cavity and oropharyngeal squamous cell carcinoma. Cancer. 2004; 101:2779-87.

Pagès F, Berger A, Camus M, et al. Effector memory T cells, early metastasis, and survival in colorectal cancer. N Engl J Med. 2005; 353(25):2654-66.

---

We claim:

1. A method for the treatment of cancer in a patient, comprising i) determining the level of CD3+ and CD16+ cell infiltration in a tumor of the patient prior to treatment, ii) detecting a level of CD3+ and CD16+ cell infiltration in the tumor of the patient higher than a reference level representative of CD3+ and CD16+ cell infiltration in tumors prior to treatment of a population of patients deriving no clinical benefit from the treatment, and iii) administering the treatment to the patient, wherein the treatment is administration of an ADCC-enhanced antibody.

2. The method of claim 1, wherein said level of CD3+ and CD16+ cell infiltration in the tumor is determined in vitro in a tumor sample taken from the patient prior to treatment.

3. The method of claim 1, wherein said reference level is determined in vitro in tumor samples taken prior to treatment from patients deriving no clinical benefit from the treatment.

4. The method of claim 1, wherein said ADCC-enhanced antibody is administered to a patient having an at least 1.2-fold, at least 1.5-fold, at least 2-fold or at least 3-fold higher level of CD3+ and CD16+ cell infiltration compared to the reference level.

5. The method of claim 1, wherein said cancer is selected from the group consisting of colorectal carcinoma, non-small cell lung cancer, and head and neck squamous cell carcinoma.

6. The method of claim 1, wherein said ADCC-enhanced antibody is a glycoengineered antibody comprising an increased proportion of non-fucosylated oligosaccharides in its Fc region, compared to a corresponding non-glycoengineered antibody.

7. The method of claim 1, wherein said ADCC-enhanced antibody is a humanized, IgG1-subclass anti-EGFR antibody comprising a) in the heavy chain variable domain a CDR1 of SEQ ID NO: 2, a CDR2 of SEQ ID NO: 3, and a CDR3 of SEQ ID NO: 4, and b) in the light chain variable domain a CDR1 of SEQ ID NO: 5, a CDR2 of SEQ ID NO: 6, and a CDR3 of SEQ ID NO: 7.

* * * * *

SEQUENCE LISTING

```
<160> NUMBER OF SEQ ID NOS: 9

<210> SEQ ID NO 1
<211> LENGTH: 328
<212> TYPE: PRT
<213> ORGANISM: Homo sapiens

<400> SEQUENCE: 1

Thr Lys Gly Pro Ser Val Phe Pro Leu Ala Pro Ser Ser Lys Ser Thr
1               5                   10                  15

Ser Gly Gly Thr Ala Ala Leu Gly Cys Leu Val Lys Asp Tyr Phe Pro
            20                  25                  30

Glu Pro Val Thr Val Ser Trp Asn Ser Gly Ala Leu Thr Ser Gly Val
        35                  40                  45

His Thr Phe Pro Ala Val Leu Gln Ser Ser Gly Leu Tyr Ser Leu Ser
    50                  55                  60

Ser Val Val Thr Val Pro Ser Ser Ser Leu Gly Thr Gln Thr Tyr Ile
65                  70                  75                  80

Cys Asn Val Asn His Lys Pro Ser Asn Thr Lys Val Asp Lys Lys Ala
                85                  90                  95

Glu Pro Lys Ser Cys Asp Lys Thr His Thr Cys Pro Pro Cys Pro Ala
            100                 105                 110

Pro Glu Leu Leu Gly Gly Pro Ser Val Phe Leu Phe Pro Pro Lys Pro
        115                 120                 125

Lys Asp Thr Leu Met Ile Ser Arg Thr Pro Glu Val Thr Cys Val Val
    130                 135                 140

Val Asp Val Ser His Glu Asp Pro Glu Val Lys Phe Asn Trp Tyr Val
145                 150                 155                 160
```

```
Asp Gly Val Glu Val His Asn Ala Lys Thr Lys Pro Arg Glu Glu Gln
            165                 170                 175
Tyr Asn Ser Thr Tyr Arg Val Val Ser Val Leu Thr Val Leu His Gln
        180                 185                 190
Asp Trp Leu Asn Gly Lys Glu Tyr Lys Cys Lys Val Ser Asn Lys Ala
        195                 200                 205
Leu Pro Ala Pro Ile Glu Lys Thr Ile Ser Lys Ala Lys Gly Gln Pro
    210                 215                 220
Arg Glu Pro Gln Val Tyr Thr Leu Pro Pro Ser Arg Asp Glu Leu Thr
225                 230                 235                 240
Lys Asn Gln Val Ser Leu Thr Cys Leu Val Lys Gly Phe Tyr Pro Ser
                245                 250                 255
Asp Ile Ala Val Glu Trp Glu Ser Asn Gly Gln Pro Glu Asn Asn Tyr
            260                 265                 270
Lys Thr Thr Pro Pro Val Leu Asp Ser Asp Gly Ser Phe Phe Leu Tyr
        275                 280                 285
Ser Lys Leu Thr Val Asp Lys Ser Arg Trp Gln Gln Gly Asn Val Phe
    290                 295                 300
Ser Cys Ser Val Met His Glu Ala Leu His Asn His Tyr Thr Gln Lys
305                 310                 315                 320
Ser Leu Ser Leu Ser Pro Gly Lys
                325

<210> SEQ ID NO 2
<211> LENGTH: 5
<212> TYPE: PRT
<213> ORGANISM: Artificial Sequence
<220> FEATURE:
<223> OTHER INFORMATION: anti-EGFR HCDR1

<400> SEQUENCE: 2

Asp Tyr Lys Ile His
1               5

<210> SEQ ID NO 3
<211> LENGTH: 17
<212> TYPE: PRT
<213> ORGANISM: Artificial Sequence
<220> FEATURE:
<223> OTHER INFORMATION: anti-EGFR HCDR2

<400> SEQUENCE: 3

Tyr Phe Asn Pro Asn Ser Gly Tyr Ser Thr Tyr Ala Gln Lys Phe Gln
1               5                   10                  15
Gly

<210> SEQ ID NO 4
<211> LENGTH: 11
<212> TYPE: PRT
<213> ORGANISM: Artificial Sequence
<220> FEATURE:
<223> OTHER INFORMATION: anti-EGFR HCDR3

<400> SEQUENCE: 4

Leu Ser Pro Gly Gly Tyr Tyr Val Met Asp Ala
1               5                   10

<210> SEQ ID NO 5
<211> LENGTH: 11
<212> TYPE: PRT
<213> ORGANISM: Artificial Sequence
```

-continued

```
<220> FEATURE:
<223> OTHER INFORMATION: anti-EGFR LCDR1

<400> SEQUENCE: 5

Arg Ala Ser Gln Gly Ile Asn Asn Tyr Leu Asn
1               5                   10

<210> SEQ ID NO 6
<211> LENGTH: 7
<212> TYPE: PRT
<213> ORGANISM: Artificial Sequence
<220> FEATURE:
<223> OTHER INFORMATION: anti-EGFR LCDR2

<400> SEQUENCE: 6

Asn Thr Asn Asn Leu Gln Thr
1               5

<210> SEQ ID NO 7
<211> LENGTH: 8
<212> TYPE: PRT
<213> ORGANISM: Artificial Sequence
<220> FEATURE:
<223> OTHER INFORMATION: anti-EGFR LCDR3

<400> SEQUENCE: 7

Leu Gln His Asn Ser Phe Pro Thr
1               5

<210> SEQ ID NO 8
<211> LENGTH: 120
<212> TYPE: PRT
<213> ORGANISM: Artificial Sequence
<220> FEATURE:
<223> OTHER INFORMATION: anti-EGFR VH

<400> SEQUENCE: 8

Gln Val Gln Leu Val Gln Ser Gly Ala Glu Val Lys Lys Pro Gly Ser
1               5                   10                  15

Ser Val Lys Val Ser Cys Lys Ala Ser Gly Phe Thr Phe Thr Asp Tyr
            20                  25                  30

Lys Ile His Trp Val Arg Gln Ala Pro Gly Gln Gly Leu Glu Trp Met
        35                  40                  45

Gly Tyr Phe Asn Pro Asn Ser Gly Tyr Ser Thr Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Ser Pro Gly Gly Tyr Tyr Val Met Asp Ala Trp Gly Gln
            100                 105                 110

Gly Thr Thr Val Thr Val Ser Ser
        115                 120

<210> SEQ ID NO 9
<211> LENGTH: 108
<212> TYPE: PRT
<213> ORGANISM: Artificial Sequence
<220> FEATURE:
<223> OTHER INFORMATION: anti-EGFR VL

<400> SEQUENCE: 9

Asp Ile Gln Met Thr Gln Ser Pro Ser Ser Leu Ser Ala Ser Val Gly
```

-continued

```
1               5                   10                  15
Asp Arg Val Thr Ile Thr Cys Arg Ala Ser Gln Gly Ile Asn Asn Tyr
            20                  25                  30

Leu Asn Trp Tyr Gln Gln Lys Pro Gly Lys Ala Pro Lys Arg Leu Ile
            35                  40                  45

Tyr Asn Thr Asn Asn Leu Gln Thr Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Phe Pro Thr
                85                  90                  95

Phe Gly Gln Gly Thr Lys Leu Glu Ile Lys Arg Thr
                100                 105
```